US009388210B2

(12) United States Patent
Covey et al.

(10) Patent No.: US 9,388,210 B2
(45) Date of Patent: Jul. 12, 2016

(54) NEUROACTIVE 17(20)-Z-VINYLCYANO-SUBSTITUTED STEROIDS, PRODRUGS THEREOF, AND METHODS OF TREATMENT USING SAME

(75) Inventors: Douglas Covey, St. Louis, MO (US); Eva Kudova, Prague (CZ)

(73) Assignee: WASHINGTON UNIVERSITY, St. Louis, MO (US)

( * ) Notice: Subject to any disclaimer, the term of this patent is extended or adjusted under 35 U.S.C. 154(b) by 123 days.

(21) Appl. No.: 14/000,519

(22) PCT Filed: Feb. 24, 2012

(86) PCT No.: PCT/US2012/026542
§ 371 (c)(1),
(2), (4) Date: Jan. 22, 2014

(87) PCT Pub. No.: WO2012/116290
PCT Pub. Date: Aug. 30, 2012

(65) Prior Publication Data
US 2014/0309443 A1 Oct. 16, 2014

Related U.S. Application Data

(60) Provisional application No. 61/446,600, filed on Feb. 25, 2011.

(51) Int. Cl.
| C07J 41/00 | (2006.01) |
| C07J 1/00 | (2006.01) |
| C07J 13/00 | (2006.01) |
| C07J 3/00 | (2006.01) |
| C07J 7/00 | (2006.01) |
| C07J 21/00 | (2006.01) |

(52) U.S. Cl.
CPC ............ *C07J 41/0094* (2013.01); *C07J 1/0011* (2013.01); *C07J 3/00* (2013.01); *C07J 7/002* (2013.01); *C07J 13/005* (2013.01); *C07J 21/008* (2013.01)

(58) Field of Classification Search
CPC .................................................. C07J 41/0094
See application file for complete search history.

(56) References Cited

U.S. PATENT DOCUMENTS

| 3,206,459 | A | | 9/1965 | Cross |
| 4,071,625 | A | | 1/1978 | Grunwell et al. |
| 4,389,345 | A | * | 6/1983 | Lenz .................... C07J 41/0094 |
| | | | | 552/505 |
| 5,925,630 | A | | 7/1999 | Upasani et al. |
| 7,781,421 | B2 | | 8/2010 | Covey et al. |
| 2002/0091112 | A1 | | 7/2002 | Menzenbach et al. |
| 2005/0176976 | A1 | | 8/2005 | Calogeropoulou et al. |
| 2006/0094696 | A1 | | 5/2006 | Leese et al. |
| 2010/0234335 | A1 | * | 9/2010 | Gravanis .................. C07J 21/00 |
| | | | | 514/173 |

FOREIGN PATENT DOCUMENTS

| DE | 2632677 A1 | 1/1978 |
| EP | 0104489 A1 | 4/1984 |
| WO | 2008151745 A1 | 12/2008 |
| WO | 2012013816 A1 | 2/2012 |
| WO | 2012083090 A2 | 6/2012 |
| WO | 2012116290 A2 | 8/2012 |

OTHER PUBLICATIONS

Dauben et al, Journal of the American Chemical Society, The Stereochemistry of Hydride Reductions, 1956, 78, pp. 2579-2581.*
Shu et al, British journal of Pharmacology, Characteristics of Concatemeric GABAA Receptors Containing alpha 4/delta Subunits Expressed Xenopus Oocytes, 2012, 165, pp. 2228-2243.*
Anderson, et al. "Anesthetic Activity of Novel Water-Soluble 2β-Morpholinyl Steroids and Their Modulatory Effects at GABA-A Receptors," J. Med. Chem., vol. 40, pp. 1668-1681 (1997).
Bandyopadhyaya, et al., "Neurosteroid analogues. 15. A comparative study of the anesthetic and GABAergic actions of alphaxalone, Δ 16-alphaxalone and their corresponding 17-carbonitrile analogues," Bioorg Med Chem Lett., vol. 20, Issue 22, pp. 6680-6684 (Nov. 15, 2010).
Berge et al., J. Pharmaceutical Sciences, 1977, 66, 1-19.
E. Stastna, et al., Neurosteroid Analogues. 16. A New Explanation for the Lack of Anesthetic Effects in Δ16-Alphaxalone and Identification of a Δ17(20) Analogue with Potent Anesthetic Activity, J. Med. Chem., 54(11), pp. 3926-3934 (2011).
Green, P. S.; Yang, S. H.; Nilsson, K. R.; Kumar, A. S.; Covey, D. F.; Simpkins, J. W. The nonfeminizing enantiomer of 17β-estradiol exerts protective effects in neuronal cultures and a rat model of cerebral ischemia. Endocrinology 2001, 142, 400-406.
Han, et al., "Neurosteroid Analogs. 3. The Synthesis and Electrophysiological Evaluation of Benz[e]indene Congeners of Neuroactive Steroids Having the 5â-Configuration," J. of Med. Chem., vol. 38(22), pp. 4548-4556 (1995).
Hu, Y. F.; Wittmer, L. L.; Kalkbrenner, M.; Evers, A. S.; Zorumski, C. F.; Covey, D. F. Neurosteroid analogues. Part 5. Enantiomers of neuroactive steroids and benz[e]indenes: total synthesis, electrophysiological effects on GABAA receptor function and anesthetic actions in tadpoles. J. Chem. Soc. Perkin Trans. 1 1997, 3665-3671.
International Search Report and Written Opinion for PCT/US2012/026542, dated Dec. 12, 2012, 14 pages.
Kaji, et al., "Synthesis of 3-epi-6, 7-dideoxyxestobergsterol A," Chem. & Pharm. Bulletin, vol. 48(10), pp. 1480-1483 (2000).

(Continued)

*Primary Examiner* — Paul A Zucker
(74) *Attorney, Agent, or Firm* — Armstrong Teasdale LLP

(57) ABSTRACT

The present disclosure is generally directed to neuroactive 17(20)-Z-vinylcyano-substituted compound of Formula (I) and (II), as referenced herein, and pharmaceutically acceptable salts thereof, for use as, for example, an anesthetic, and/or in the treatment of disorders relating to GABA function and activity. The present disclosure is further directed to pharmaceutical compositions comprising such compounds.

9 Claims, 14 Drawing Sheets

(56) References Cited

OTHER PUBLICATIONS

Katona, B. W.; Krishnan, K.; Cai, Z. Y.; Manion, B. D.; Benz, A.; Taylor, A.; Evers, A. S.; Zorumski, C. F.; Mennerick, S.; Covey, D. F. Neurosteroid analogues. 12. Potent enhancement of GABA-mediated chloride currents at GABAA receptors by ent-androgens. Eur. J. Med. Chem. 2008, 43, 107-113.
Nilsson, K. R.; Zorumski, C. F.; Covey, D. F. Neurosteroid analogues. 6. The synthesis and GABAA receptor pharmacology of enantiomers of dehydroepiandrosterone sulfate, pregnenolone sulfate, and ($3\alpha,5\beta$)-3-hydroxypregnan-20-one sulfate. J. Med. Chem. 1998, 41, 2604-2613.
Qian & Covey, "The efficient and enantiospecific total synthesis of cyclopenta[b]phenanthrenes structurally related to neurosteroids," Adv. Syn. & Cata., vol. 352 (11-12), pp. 2057-2061 (2010).
Rychnovsky & Mickus, "Synthesis of ent-cholesterol, the unnatural enantiomer," J. of Org. Chem., vol. 57(9), pp. 2732-2736 (1992).
Santaniello & Caspi, "Reduction of certain steroidal 19-sulfonic esters with metal hydrides," J. of Ster. Biochem., vol. 7 (3), pp. 223-227 (1976).
Sarett, L.H., A new method for the preparation of 17(alpha)-hydroxy-20-ketopregnanes. J. Am. Chem. Soc., 70: 1454-8 (1948).
Scaglione, et al., "Neurosteroid Analogues. 14. Alternative Ring System Scaffolds: GABA Modulatory and Anesthetic Actions of Cyclopenta[b]phenanthrenes and Cyclopenta[b]anthracenes," J. Med. Chem., vol. 51, pp. 1309-1318 (2008).
Shu Hong-Jin et al. Characteristics of concatemeric GABAA receptors containing α4/σ subunits expressed in Xenopus oocytes. British Journal of Pharmacology, 2012, 165, pp. 2228-2243.
Stastna, E.; Rath, N. P.; Covey, D. F. The use of symmetry in enantioselective synthesis: Four pairs of chrysene enantiomers prepared from 19-nortestosterone. Org. Biomol. Chem. 2011, 9, 4685-4694.
Upasani, et al., "$3\alpha$-Hydroxy-$3\beta$-(phenylethynyl-$5\beta$-pregnan-20-ones: Synthesis and Pharmacological Activity of Neuroactive Steroids with High Affinity for GABA-A Receptors," J. Med. Chem., vol. 40, pp. 73-84 (1997).
Wu, Pharmaceuticals (2009) 2:77-81.
Jiang, X., et al., Neurosteroid analogues. 9. Conformationally constrained pregnanes: structure-activity studies of 13,24-cyclo-18,21-dinorcholane analogues of the GABA modulatory and anesthetic steroids ($3\alpha$, $5\alpha$)- and ($3\alpha$, $5\alpha$)-3-hydroxypregnan-20-one. J. Med., 46: 5334-48 (2003).
Ruzicka, et al., "Steroids and sex hormones. CXXXIX. The relation between constitution and odor of steroids. Methylandrostane and allopregnane derivatives," Helvetica Chimica Acta, vol. 30(3), pp. 867-878 (1947).
Heard, et al., "Steroids. VII. Preparation of androstan-3($\beta$)-ol-7-one from dehydroisoandrosterone," Journal of Biological Chemistry, vol. 165, pp. 677-685 (1646).
Fajkos, et al., "Steroids. XXIII. Synthesis and configuration of the two stereoisomeric $3\beta$-hydroxy-16-acetylandrostanes," Chemicke Listy pro Vedu a Prumysl, vol. 50, pp. 791-799 (1956).
International Search Report and Written Opinion issued for International Application No. PCT/US2014/016405 (Jul. 16, 2014).

Cerny, et al., "Syntheses of 19-[O-(carboxymethyl)oxime] haptens of epipregnanolone and pregnanolone," Steroids, vol. 71(2), pp. 120-128 (2006).
Cerny, et al., "Synthetic approach to 5alpha-pregnanolone 19-[O-(carboxymethyl) oxime] derivatives," Collection of Czechoslovak Chemical Communications, vol. 69(9), pp. 1805-1817 (2004).
Wicha, et al., "Transformations of steroidal neopentyl systems. II. Migration of acetate from the 3beta- to the 19-hydroxyl in delta 5 and A/B-trans steroids," Canadian Journal of Chemistry, vol. 45(7), pp. 707-711 (1967).
Hill, et al., "Photochemische Reaktionen. 32 Mitteilung. UV-Bestrahlung von gesattigten und beta,gamma-ungesattigten, homoallylisch konjugierten steroidaldehyden," Helvetica Chimica Acta, vol. 49(1), pp. 292-311 (1946).
Wicha, et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs," Journal of Organic Chemistry, vol. 38(7), pp. 1280-1283 (1973).
Wicha, et al., "Transformations of steroidal neopentyl systems. V. Synthesis and proof of the configuration of 19a-methyl-19S-alcohols," Journal of the Chemical Society [Section] C: Organic, vol. 6, pp. 947-951 (1969).
Wicha, et al., "Transformations of steroidal neopentyl systems. IV. Stereochemistry of products of reaction of methyllithium with steroidal delta5-19-aldehydes," Journal of the Chemical Society [Section] C: Organic, vol. 14, pp. 1740-1746 (1968).
Caspi, et al., "Stereochemistry of 19-hydroxy-19alpha-methyl steroids," Chemical Communications, vol. 7, pp. 209-210 (1966).
Knox, et al., "Steroids. CCLXXVIII. Reductions of 19-substituted androst-4-en-3-ones and related compounds," Journal of Organic Chemistry, vol. 30(7), pp. 2198-2205 (1965).
International Search Report and Written Opinion issued for International Application No. PCT/US2013/076214 (Jun. 5, 2014).
Bandyopadhyaya, et al., "Neurosteroid analogues. 15. A comparative study of the anesthetic and GABAergic actions of alphaxalone, delta 16-alphaxalone and their corresponding 17-carbonitrile analogues," Bioorg Med Chem Lett., vol. 20, Issue 22, pp. 6680-6684 (Nov. 15, 2010).
Hauser, et al., "Steroids. CCV. Fragmentations and intramolecular abstractions of tertiary hydrogen atoms by primary oxy radicals with fixed reaction centers," Helv. Chim. Acta, vol. 47, pp. 1961-1979 (1964).
Qian, et al., "Neurosteroid Analogues, 18. Structure-Activity Studies of ent-Steroid Potentiators of γ-Aminobutyric Acid Type A Receptors and Comparison of Their Activities with Those of Alphaxalone and Allopregnanolone," J. of Med. Chem., vol. 57(1), pp. 171-190 (2014).
Ruzicka, et al., "Steroids and sex hormones. CXXXIX. The relation between constitution and odor of steroids. Methylandrostane and allopregnane derivatives," Helvetica Chimica Acta, vol. 30, pp. 867-878 (1947).
Spiegel et al., "Use of Nonaqueous Solvents in Parenteral Products," J. of Pharm. Sciences, vol. 52, No. 10, pp. 917-927 (1963).
Stastna, et al., "Stereoselectivity of sodium borohydride reduction of saturated steroidal ketones utilizing conditions of Luche reduction," Steroids, vol. 75(10), pp. 721-725 (2010).

* cited by examiner a) MOMCl, Hunig's base, CH$_2$Cl$_2$
b) PhN(SO$_2$CF$_3$)$_2$, KHMDS, THF, -78 °C
c) NaCN, CuI, Pd(PPh$_3$)$_4$, MeCN
d) DIBALH, toluene, CH$_2$Cl$_2$, -78 °C
e) PCC, CH$_2$Cl$_2$
f) EtOH, 6 N HCl
g) H$_2$ (60 psi), Lindlar's catalyst (5%), EtOAc.

Scheme 2

6a: Ry = CN; Rz = H
6b: Ry = H; Rz = CN

5c a) NaH, diethyl(cyanomethyl)phosphonate, THF, 0 to 20°C
b) H₂ (60 psi), Pd/C, EtOAc/EtOH Scheme 6

15a: $R_y$ = CN; $R_z$ = H
15b: $R_y$ = H; $R_z$ = CN

Scheme 7

16a: R$_y$ = CN; R$_z$ = H
16b: R$_y$ = H; R$_z$ = CN

NEUROACTIVE 17(20)-Z-VINYLCYANO-SUBSTITUTED STEROIDS, PRODRUGS THEREOF, AND METHODS OF TREATMENT USING SAME

CROSS-REFERENCE TO RELATED APPLICATIONS

This application is a U.S. National Phase Patent Application of International Application Serial Number PCT/US2012/026542, filed Feb. 24, 2012, which is incorporated herein in its entirety, and which claims priority from U.S. Provisional Patent Application Ser. No. 61/446,600, filed Feb. 25, 2011, which is also incorporated herein in its entirety.

GOVERNMENT SUPPORT

The claimed subject matter was developed with Government support under NIH Grant # GM47969, awarded by the National Institute of Health. Accordingly, the Government has certain rights in the claimed subject matter.

BACKGROUND OF THE DISCLOSURE

The present disclosure is generally directed to novel compounds having utility as an anesthetic and/or in the treatment of disorders relating to GABA function and activity. More specifically, the present disclosure is directed to steroids having a 17(20)-Z-vinylcyano-substituted tetracyclic structure that are neuroactive and suitable for use as an anesthetic, as well as pharmaceutically acceptable salts and prodrugs thereof, and pharmaceutical compositions containing them.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. For example, it is now widely accepted that the intravenous anesthetic alphaxalone (Compound 1, below) causes general anesthesia in humans because it allosterically increases chloride currents mediated by GABA acting at $GABA_A$ receptors in the brain. However, the various structural features that enable this compound to function in the way it does have, to-date, not been fully understood. For example, in contrast to alphaxalone, $\Delta^{16}$-alphaxalone (Compound 2, below), has been observed to have greatly diminished allosteric activity at $GABA_A$ receptors and is not used as an intravenous general anesthetic in humans.

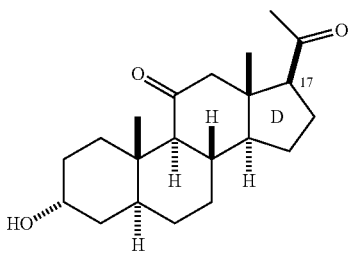

Compound 1

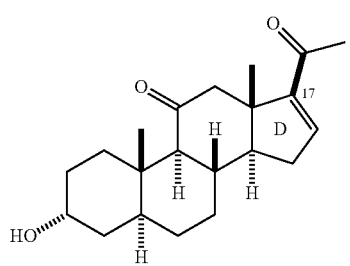

Compound 2

The difference in performance of these two compounds, which some have attributed to the presence of the carbon-carbon double bond in the D-ring, has attracted the attention of many researchers. In fact, recently, it was determined that the effect this double bond has on anesthetic activity may depend on the group attached at C-17 on the D-ring. (See Bandyopadhyaya, A. K., et al., "Neurosteroid analogues. 15. A comparative study of the anesthetic and GABAergic actions of alphaxalone, $\Delta^{16}$-alphaxalone and their corresponding 17-carbonitrile analogues. Bioorg. Med. Chem. Lett., 20: 6680-4 (2010))

In addition to anesthetic properties, neuroactive steroids may be used to treat disorders related to GABA function. For example, neuroactive steroids, such as progesterone, may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating steroids would exhibit anxiolytic effects. Neuroactive steroids may also be used to treat depression, given that accumulating evidence suggests that patients with major depression have decreased levels of GABAergic neurosteroids and that certain treatments for depression alter levels of these steroids. Although GABA is not typically thought to play a critical role in the biology of depression, there is evidence that low GABAergic activity may predispose one to mood disorders. Finally, inhibition of NMDA receptors and enhancement of $GABA_A$ receptors appear to play important roles in mediating the acute effects of ethanol in the nervous system, while related studies suggest that GABAergic neurosteroids may be involved in some of the pharmacological effects of ethanol and that neuroactive steroids may be useful in treating ethanol withdrawal.

In view of the foregoing, it is clear that there are a number of potentially advantageous uses for neurosteroids. As a result, there is a continuing need for the further synthesis and understanding of new neuroactive steroids, particularly those having utility as an anesthetic and/or in the treatment of a disorder relating to GABA function and activity.

SUMMARY OF THE DISCLOSURE

In one aspect, the present disclosure is directed to a compound having a structure of Formula (I):

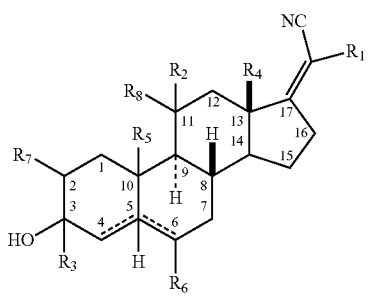
(I)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_3$ is H, optionally substituted $C_1$-$C_4$ alkyl, optionally substituted $C_2$-$C_4$ alkene, optionally substituted $C_2$-$C_4$ alkyne, or optionally substituted aryl;
$R_4$ and $R_5$ are each independently selected from H and unsubstituted $C_1$-$C_4$ alkyl;
$R_6$ is H, optionally substituted $C_1$-$C_4$ alkyl, optionally substituted $C_1$-$C_4$ alkoxy;
$R_7$ is H, optionally substituted $C_1$-$C_4$ alkoxy, or an optionally substituted morpholinyl ring;
$R_8$, when present, is H or optionally substituted $C_1$-$C_4$ alkyl; and,
- - - denotes an optional, additional C—C bond, resulting in either a C=C bond between $C_4$-$C_5$ or $C_5$-$C_6$, with the proviso that when present, the $C_5$—H substituent is not present.

The present disclosure is further directed to a pharmaceutically acceptable salt of the noted compounds, or alternatively to prodrugs thereof. In one particular embodiment, the present disclosure is directed to a compound having a structure of Formula (II):

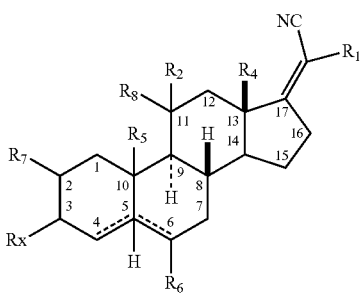
(II)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_x$ is =O, OH, or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration;
$R_4$ and $R_5$ are each independently selected from H and unsubstituted $C_1$-$C_4$ alkyl;
$R_6$ is H, optionally substituted $C_1$-$C_4$ alkyl, or optionally substituted $C_1$-$C_4$ alkoxy;
$R_7$ is H, optionally substituted $C_1$-$C_4$ alkoxy, or an optionally substituted morpholinyl ring;
$R_8$, when present, is H or optionally substituted $C_1$-$C_4$ alkyl; and,
- - - denotes an optional, additional C—C bond, resulting in either a C=C bond between $C_4$-$C_5$ or $C_5$-$C_6$, with the proviso that when present, the $C_5$—H substituent is not present.

The present disclosure is still further directed to a pharmaceutical composition comprising a therapeutically effective amount of one or more of the above-noted steroids, or pro-drugs, or pharmaceutically acceptable salts thereof, and optionally a pharmaceutically acceptable carrier. The present disclosure also provides kits comprising steroids, salts thereof, pro-drugs thereof, and/or pharmaceutical compositions thereof.

The present disclosure further provides methods of inducing anesthesia in a subject in need thereof, the method comprising administering to the subject a therapeutically effective amount of one or more of the above-noted steroids, or pro-drugs, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

DETAILED DESCRIPTION OF CERTAIN EMBODIMENTS

Figure 1:
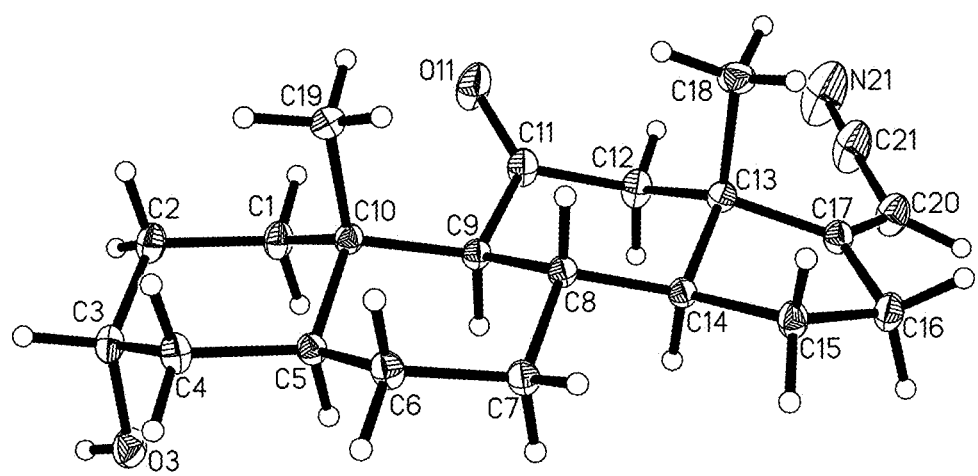
FIG. 1 is a projection plot (50% thermal ellipsoids) of the X-ray crystal structure of Compound 6a disclosed herein.

In accordance with the present disclosure, it has been discovered that compounds having a 17(20)-Z-vinylcyano-substituted steroid structure, and more specifically a 3α-hydroxy-17(20)-Z-vinylcyano-substituted tetracyclic steroid structure, are neuroactive and are also suitable for use as anesthetics and in the treatment of disorders associated with GABA function, as well as pharmaceutically acceptable salts and prodrugs thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1. Steroid Structure

Generally speaking, the steroid of the present disclosure has a tetracyclic, fused ring structure, such as a cyclopenta[a] phenanthrene ring system (an embodiment of which is illustrated and discussed in greater detail below), wherein the $C_3$-position of the A ring has a hydroxyl substituent, preferably in the α-position, and the $C_{17}$-position of the D ring has a vinyl-cyano (e.g., =CH(CN)) group, preferably in the Z-configuration, attached thereto. Notably, and as further detailed herein below, it has surprisingly been discovered that the activity of the steroids of the present disclosure are at least in part a function of the orientation or configuration of the carbon-carbon double bond of which $C_{17}$ is a part. More specifically, and as further illustrated below, it has been discovered that when this carbon-carbon double bond is in the Z-configuration (or cis-configuration), and further when the CN group is on the $C_{13}$ side of the molecule, the activity of the compound is notably higher, as compared to the alternative configuration (i.e., when the CN group is on the $C_{16}$ side of the molecule).

For example, comparison of the $IC_{50}$ values of the Compound 6a (the Z isomer) with Compound 6b (the E isomer) indicates that interchanging the relative positions of the C-20 substituents (H, CN) has a large effect on [$^{35}$S]-TBPS displacement potency. Compound 6a was about 17-fold more potent at displacing [$^{35}$S]-TBPS than Compound 6b. A comparison of the $IC_{50}$ values for Compounds 6a, 6b and 5c shows the effect that hydrogenation of the $\Delta^{17(20)}$ double bond present in Compound 6a and 6b has on binding potency. The change in conformation of the D-ring and the loss of the steric restraint imposed by the $\Delta^{17(20)}$ double bond increased the $IC_{50}$ value of Compound 5c about eight-fold relative to Compound 6a, and decreased the $IC_{50}$ value about twofold relative to Compound 6b. This disparity in displacement potency between Z and E isomers has also been observed in other 17-vinylcyano compounds studied, the Z isomer being about 10- to 20-fold more potent than the E isomer.

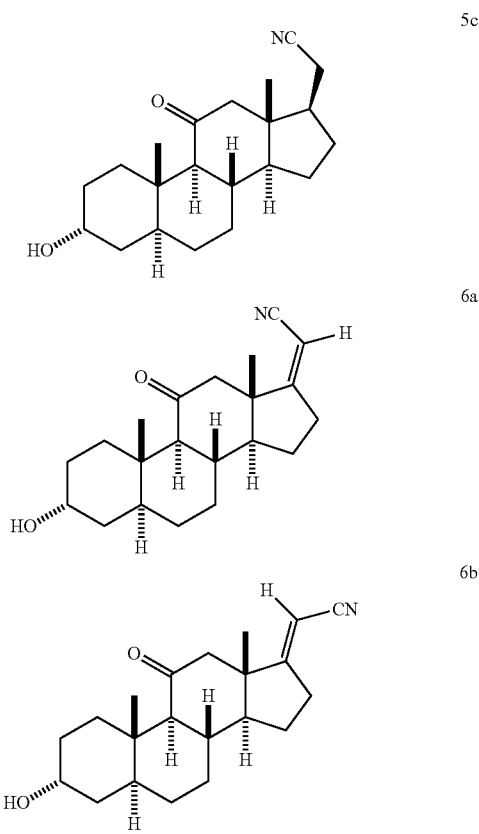

More particularly, however, the present disclosure is directed, in certain embodiments, to a steroid having the structure of Formula (I):

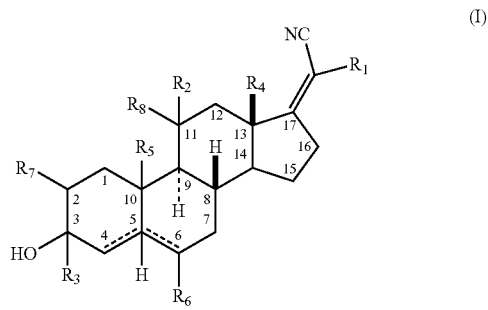

or a pharmaceutically acceptable salt thereof;

wherein:

$R_1$ is H;

$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;

$R_3$ is H, optionally substituted $C_1$-$C_4$ alkyl, optionally substituted $C_2$-$C_4$ alkene, optionally substituted $C_2$-$C_4$ alkyne, or optionally substituted aryl;

$R_4$ and $R_5$ are each independently selected from H and unsubstituted $C_1$-$C_4$ alkyl;

$R_6$ is H, optionally substituted $C_1$-$C_4$ alkyl, or optionally substituted $C_1$-$C_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl; and,

- - - denotes an optional, additional C—C bond, resulting in either a C=C bond between $C_4$-$C_5$ or $C_5$-$C_6$, with the proviso that when present, the $C_5$—H substituent is not present.

As generally defined above, $R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present. In certain embodiments, $R_2$ is =O and $R_8$ is not present. In certain embodiments, $R_2$ is H. In certain embodiments, $R_2$ is $OR_a$. In certain embodiments, $R_2$ is $OR_a$ and $R_a$ is optionally substituted $C_1$, $C_2$, $C_3$, or $C_4$ alkyl (e.g., methyl, ethyl), optionally substituted benzyl, or $C_1$, $C_2$, $C_3$, or $C_4$ alkyl substituted with O-aryl, such as O-benzyl. In certain embodiments, $R_2$ is $OR_a$ and $R_a$ is optionally substituted aryl. In certain embodiments, $R_2$ is $OR_a$ and $R_a$ is H.

As generally defined above, $R_3$ is H, optionally substituted $C_1$-$C_4$ alkyl, optionally substituted $C_2$-$C_4$ alkene, optionally substituted $C_2$-$C_4$ alkyne, or optionally substituted aryl. In certain embodiments, $R_3$ is H. In certain embodiments, $R_3$ is optionally substituted $C_1$, $C_2$, $C_3$ or $C_4$ alkyl (e.g., methyl, ethyl, trifluoromethyl, difluoromethyl). In certain embodiments, $R_3$ is methyl. In certain embodiments, $R_3$ is trifluoromethyl. In certain embodiments, $R_3$ is optionally substituted $C_2$, $C_3$ or $C_4$ alkene (e.g., optionally substituted allyl). In certain embodiments, $R_3$ is optionally substituted $C_2$, $C_3$, or $C_4$ alkyne (e.g., optionally substituted acetylene or optionally substituted propargyl). In certain embodiments, $R_3$ is optionally substituted aryl (e.g., optionally substituted phenyl, such as phenyl substituted with OH, methyl, or $COR_c$, where $R_c$ is optionally substituted $C_1$-$C_{22}$ alkyl or optionally substituted $C_2$-$C_{22}$ alkenyl, including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl). In certain embodiments, $R_3$ is in the alpha (down) position. In certain embodiments, $R_3$ is in the beta (up) position.

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is H or unsubstituted $C_1$-$C_4$ alkyl. In certain embodiments, $R_5$ is H. In certain embodiments, $R_5$ is unsubstituted $C_1$, $C_2$, $C_3$ or $C_4$ alkyl (e.g., methyl, ethyl, n-propyl, isopropyl, or n-butyl). In certain embodiments, $R_5$ is in the beta (up) position.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl). In certain embodiments, $R_6$ is optionally substituted $C_1$, $C_2$, $C_3$ or $C_4$ alkoxy (e.g., methoxy, ethoxy, n-propyloxy, isopropyloxy, or n-butoxy). In certain embodiments, when $R_6$ is a non-hydrogen group, $R_6$ is in the alpha (down) position. In certain embodiments, when $R_6$ is a non-hydrogen group, $R_6$ is in the beta (up) position.

As generally defined above, $R_7$ is H, optionally substituted $C_1$-$C_4$ alkoxy, or an optionally substituted morpholinyl ring. In certain embodiments, $R_7$ is H. In certain embodiments, $R_7$ is optionally substituted $C_1$, $C_2$, $C_3$ or $C_4$ alkoxy (e.g., methoxy, ethoxy, n-propyloxy, isopropyloxy, or n-butoxy). In certain embodiments, $R_7$ is an optionally substituted morpholinyl ring. In certain embodiments, when $R_7$ is a non-hydrogen group, $R_7$ is in the alpha (down) position. In certain embodiments, when $R_7$ is a non-hydrogen group, $R_7$ is in the beta (up) position.

As generally defined above, $R_8$, when present, is H or optionally substituted $C_1$-$C_4$ alkyl. In certain embodiments, $R_8$ is H. In certain embodiments, $R_8$ is $C_1$, $C_2$, $C_3$ or $C_4$ optionally substituted alkyl (e.g., methyl). In certain embodiments, when $R_8$ is optionally substituted $C_1$-$C_4$ alkyl, $R_8$ is in the alpha (down) position. In certain embodiments, when $R_8$ is optionally substituted $C_1$-$C_4$ alkyl, $R_8$ is in the beta (up) position.

In certain embodiments, $R_2$ and $R_8$ are both H. In certain embodiments, $R_2$ is $OR_a$ and $R_8$ is H.

As generally defined above, - - - denotes an optional, additional C—C bond, resulting in either a C=C bond between $C_4$-$C_5$ or $C_5$-$C_6$, with the proviso that when present, the $C_5$—H substituent is not present. In certain embodiments, the additional C—C bond is absent, and the hydrogen at $C_5$ is in the alpha or beta position. In certain embodiments, the additional C—C bond is absent, and the hydrogen at $C_5$ is in the alpha (down) position. In certain embodiments, the additional C—C bond is absent, and the hydrogen at $C_5$ is in the beta (up) position. In certain embodiments, - - - denotes an additional C—C bond, resulting in a C=C bond between $C_4$-$C_5$. In certain embodiments, - - - denotes an additional C—C bond, resulting in a C=C bond between $C_5$-$C_6$.

It is to be noted that the present disclosure contemplates and is intended to encompass all of the various combinations and permutations (i.e., combinations of substituent options, locations and stereochemical configurations) possible here.

For example, in various embodiments, compounds of the present disclosure may be selected from among those encompassed by the structure of Formula (I), wherein $R_2$ is =O; alternatively, $R_2$ may be H and $R_8$ is H (e.g., $C_{11}$ thus having two hydrogen atoms bound thereto as substituents). In certain embodiments, $R_2$ may be $OR_a$, wherein $R_a$ is methyl, optionally substituted benzyl, or $C_1$-$C_4$ alkyl substituted with O-aryl, such as O-benzyl. In certain embodiments, $R_3$ may be H, methyl, trifluoromethyl, or substituted aryl (e.g., substituted phenyl, which in turn may be optionally substituted such as, for example, with OH, methyl, or $COR_c$, where $R_c$=$C_1$-$C_4$ alkyl); further, when $R_3$ is something other than H, $R_3$ is preferably in the β-position. In certain embodiments, each of $R_4$, $R_5$ and $R_6$ are independently selected from H and methyl, $R_5$ being in the β-configuration and $R_6$ optionally being in the α-configuration or β-configuration (e.g., when $R_6$ is methyl). In certain embodiments, $R_7$ is selected from H, methoxy, ethoxy, and an unsubstituted morpholinyl ring; further, when $R_7$ is something other than H, $R_7$ is preferably in the β-position. In certain embodiments, $R_8$, when present, is selected from H or optionally substituted $C_1$-$C_4$ alkyl. In certain embodiments, $R_8$ is methyl (e.g., methyl in the alpha-configuration).

In certain embodiments, the $C_5$—H is in the alpha configuration and the $R_5$ is, for example, a methyl group in the beta configuration. In certain embodiments, the C5—H is in the beta configuration and $R_5$ is, for example, a methyl group in the beta configuration. In certain embodiments, $R_6$ is H. In certain embodiments, $R_4$ is methyl. In certain embodiments, $R_2$ is =O or methoxy.

Accordingly, as noted, the steroid of Formula (I) may encompass a number of various structures in accordance with the present disclosure.

In certain embodiments, wherein $R_1$ is H, $R_3$ is in the beta position, $R_4$ is methyl, $R_5$ is methyl in the beta position, and $R_6$ is H, provided is a compound of Formula (I-a):

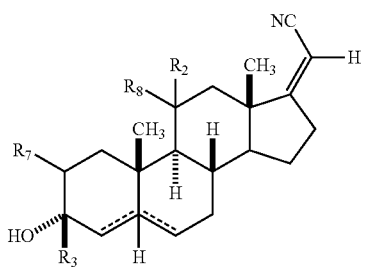

(I-a)

or a pharmaceutically acceptable salt thereof, wherein - - -, $R_2$, $R_3$, $R_7$ and $R_8$ are as defined herein. In certain embodiments, each instance of - - - is absent and $C_5$—H is in the alpha position. In certain embodiments, each instance of - - - is absent and $C_5$—H is in the beta position.

In certain embodiments of Formula (I-a), wherein $R_2$ is =O and $R_8$ is absent, provided is a compound of Formula (I-b):

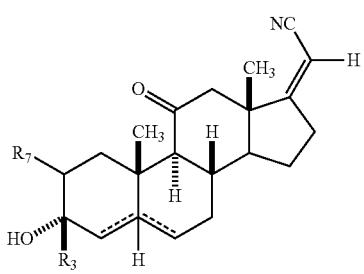

(I-b)

or a pharmaceutically acceptable salt thereof, wherein - - -, $R_3$ and $R_7$ are as defined herein. In certain embodiments, each instance of - - - is absent and $C_5$—H is in the alpha position. In certain embodiments, each instance of - - - is absent and $C_5$—H is in the beta position.

In certain embodiments of Formula (I-a), wherein $R_2$ is H and $R_8$ is H, provided is a compound of Formula (I-c):

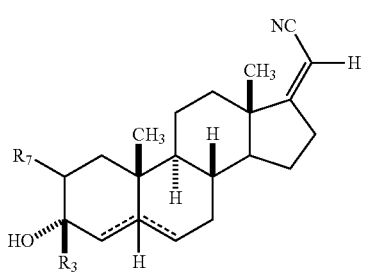

(I-c)

or a pharmaceutically acceptable salt thereof, wherein - - -, $R_3$ and $R_7$ are as defined herein. In certain embodiments, each instance of - - - is absent and $C_5$—H is in the alpha position. In certain embodiments, each instance of - - - is absent and $C_5$—H is in the beta position.

In certain embodiments of Formula (I-a), wherein $R_2$ is $OR_a$ and $R_8$ is H, provided is a compound of Formula (I-d):

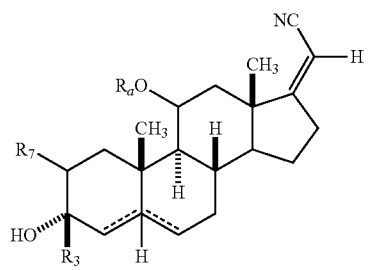

(I-d)

or a pharmaceutically acceptable salt thereof, wherein - - -, $R_3$, $R_7$, and $R_a$ are as defined herein. In certain embodiments, each instance of - - - is absent and $C_5$—H is in the alpha position. In certain embodiments, each instance of - - - is absent and $C_5$—H is in the beta position.

In certain embodiments of Formula (I-a), wherein $R_7$ is H, provided is a compound of Formula (I-e):

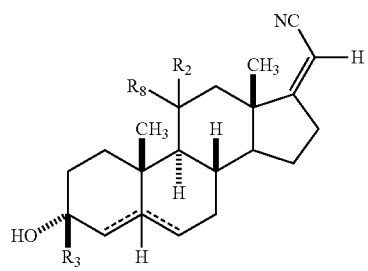

(I-e)

or a pharmaceutically acceptable salt thereof, wherein - - -, $R_2$, $R_3$, and $R_8$ are as defined herein. In certain embodiments, each instance of - - - is absent and $C_5$—H is in the alpha position. In certain embodiments, each instance of - - - is absent and $C_5$—H is in the beta position.

In certain embodiments of Formula (I-a), wherein each instance of - - - is absent and $C_5$—H is in the alpha position, provided is a compound of Formula (I-f):

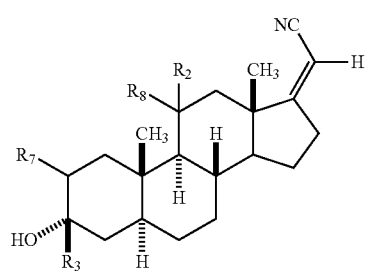

(I-f)

or a pharmaceutically acceptable salt thereof, wherein $R_2$, $R_3$, $R_7$ and $R_8$ are as defined herein.

In certain embodiments of Formula (I-f), wherein $R_7$ is H, provided is a compound of Formula (I-g):

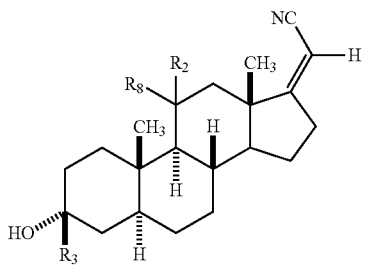
(I-g)

or a pharmaceutically acceptable salt thereof, wherein $R_2$, $R_3$, and $R_8$ are as defined herein.

In certain embodiments of Formula (I-f), wherein $R_2$ is =O, provided is a compound of Formula (I-h):

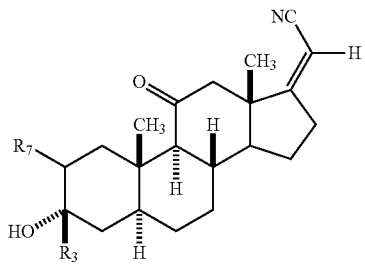
(I-h)

or a pharmaceutically acceptable salt thereof, wherein $R_3$ and $R_7$ are as defined herein.

In certain embodiments of Formula (I-f), wherein $R_2$ is $OR_a$, provided is a compound of Formula (I-i):

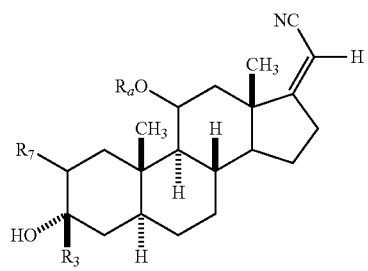
(I-i)

or a pharmaceutically acceptable salt thereof, wherein $R_a$, $R_3$, and $R_7$ are as defined herein.

In certain embodiments of Formula (I-a), wherein - - - represents an additional C—C bond, resulting in a C=C bond between $C_4$-$C_5$ provided is a compound of Formula (I-j):

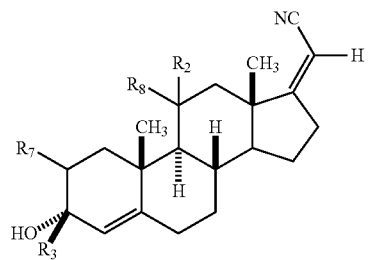
(I-j)

or a pharmaceutically acceptable salt thereof, wherein $R_3$, $R_2$, $R_7$ and $R_8$ are as defined herein.

In certain embodiments of Formula (I-a), wherein - - - represents an additional C—C bond, resulting in a C=C bond between $C_5$-$C_6$ provided is a compound of Formula (I-k):

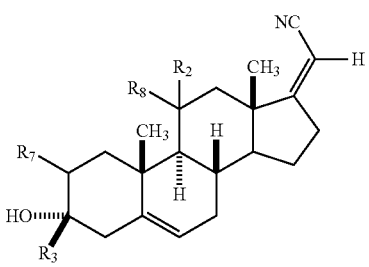
(I-k)

or a pharmaceutically acceptable salt thereof, wherein $R_3$, $R_2$, $R_7$ and $R_8$ are as defined herein.

Exemplary compounds of Formula (I) include, but are not limited to:

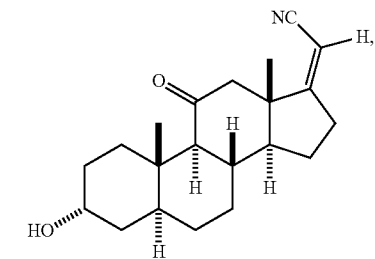

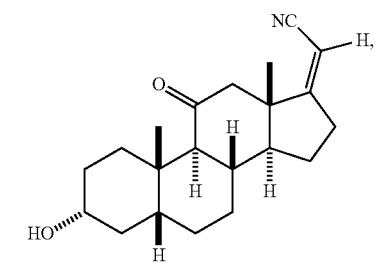

-continued
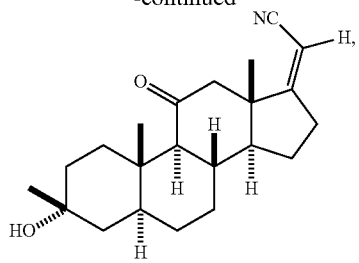
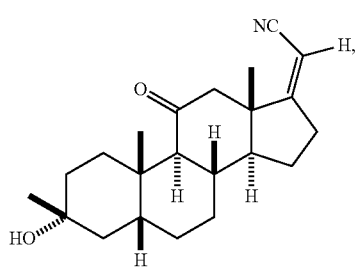
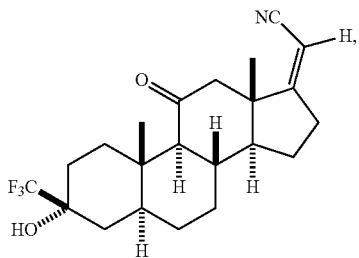
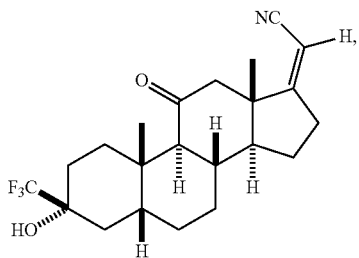
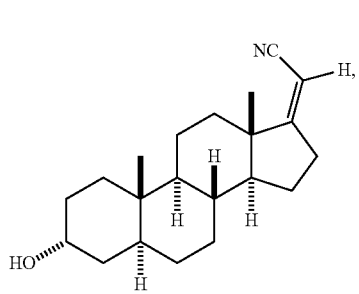
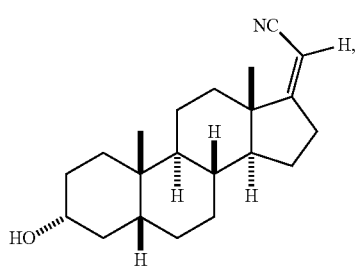
-continued
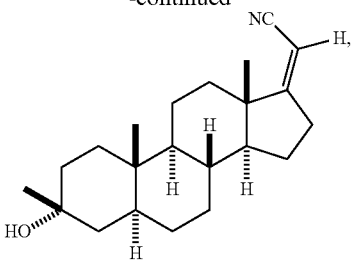
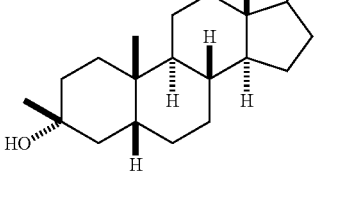
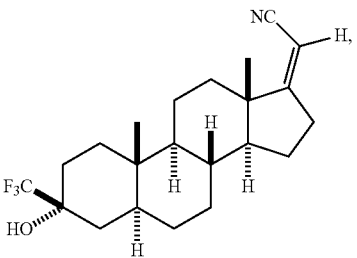
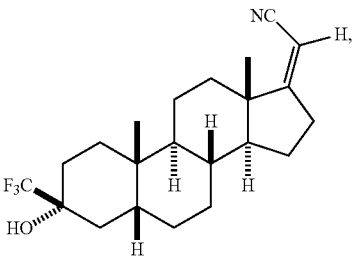
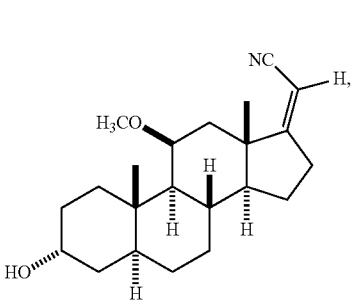
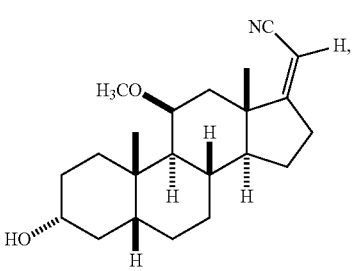

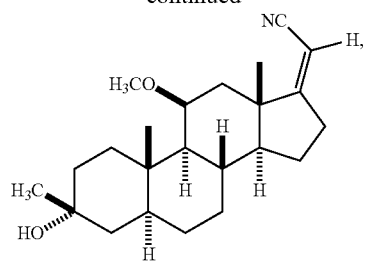
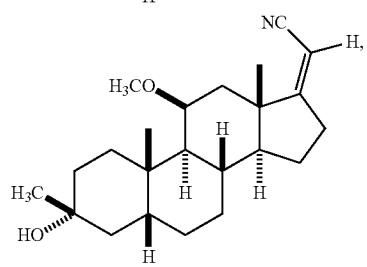
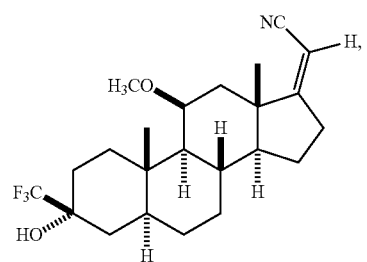
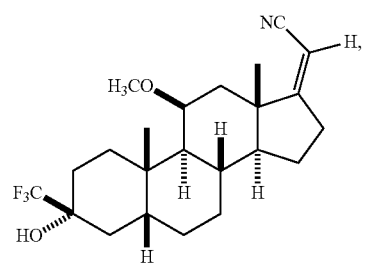
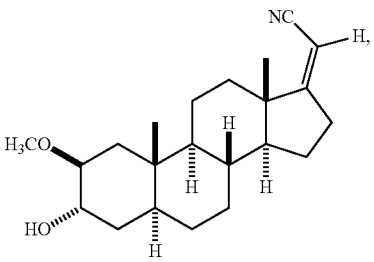
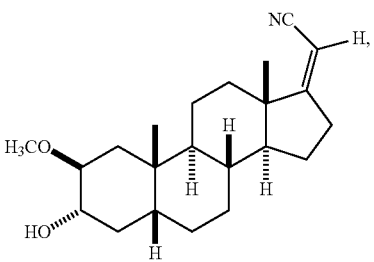
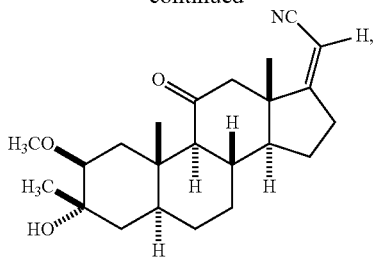
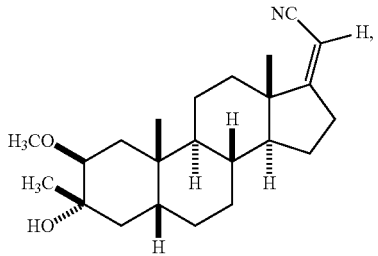
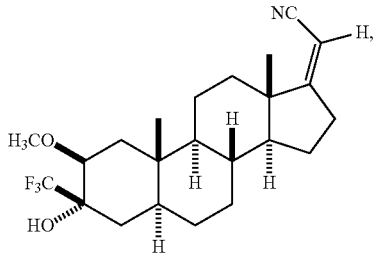
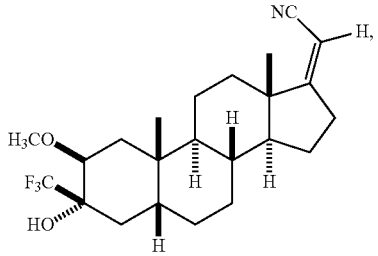
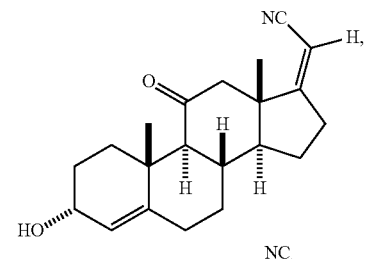
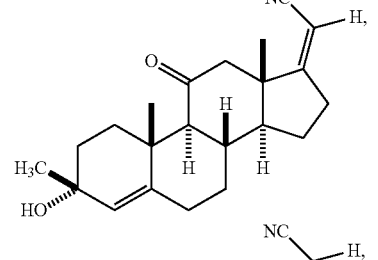
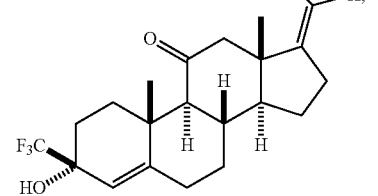

-continued
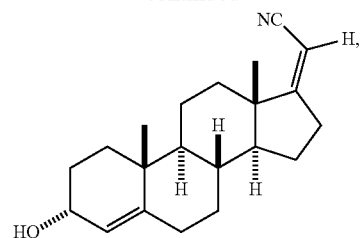
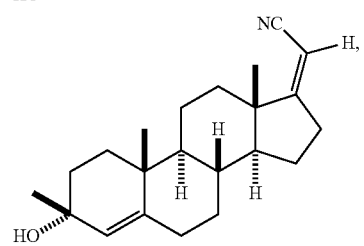
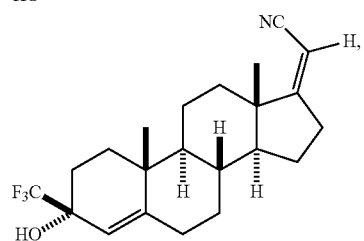
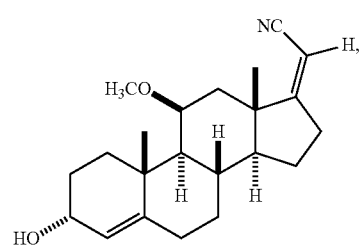
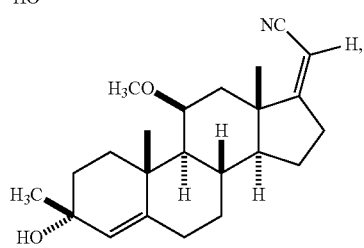
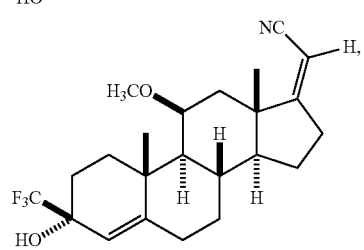
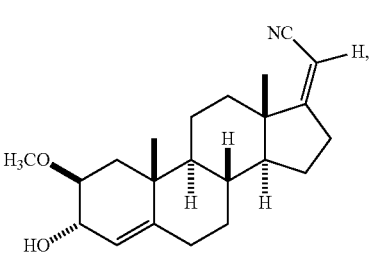
-continued
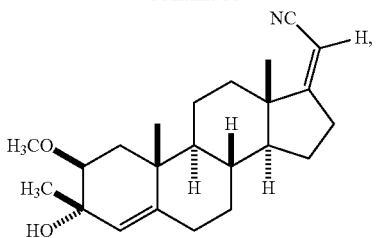
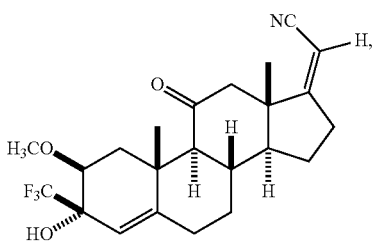
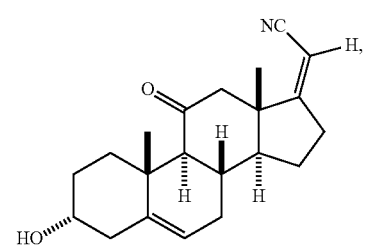
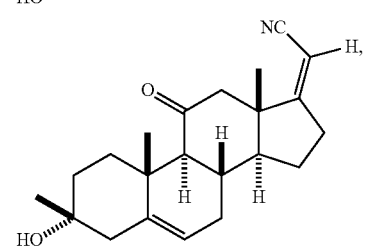
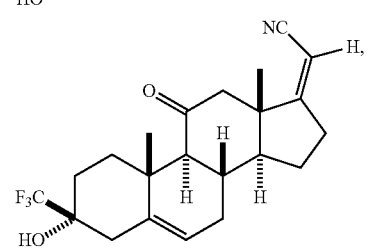
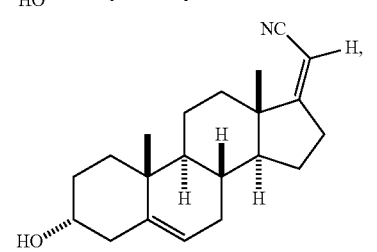
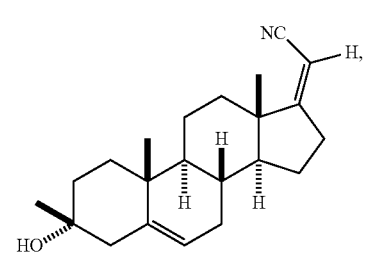

-continued

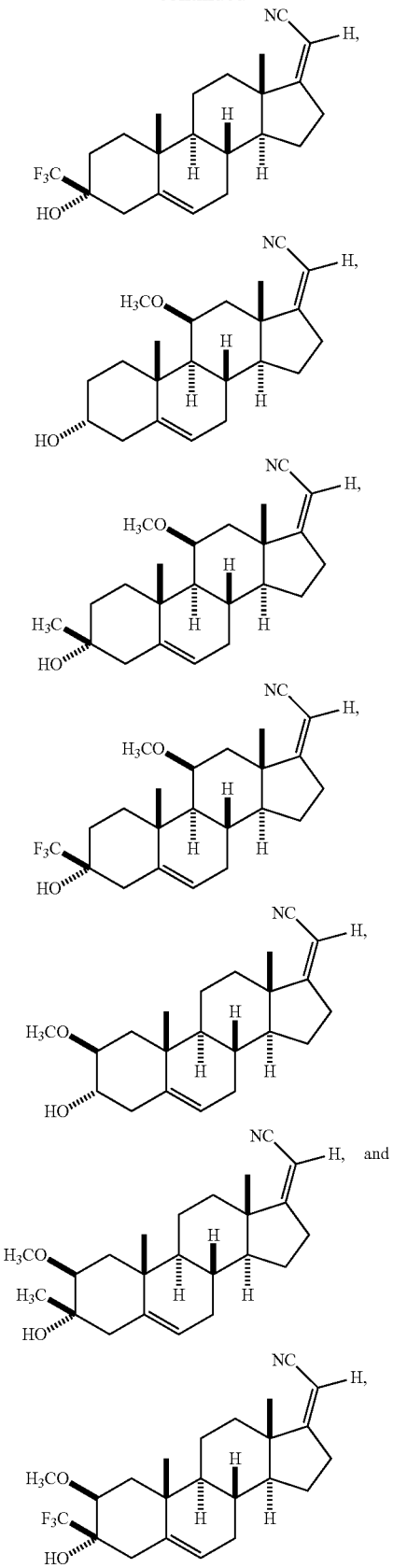

and pharmaceutically acceptable salts thereof.

In certain embodiments, the steroid of Formula (I) is selected from the group consisting of:

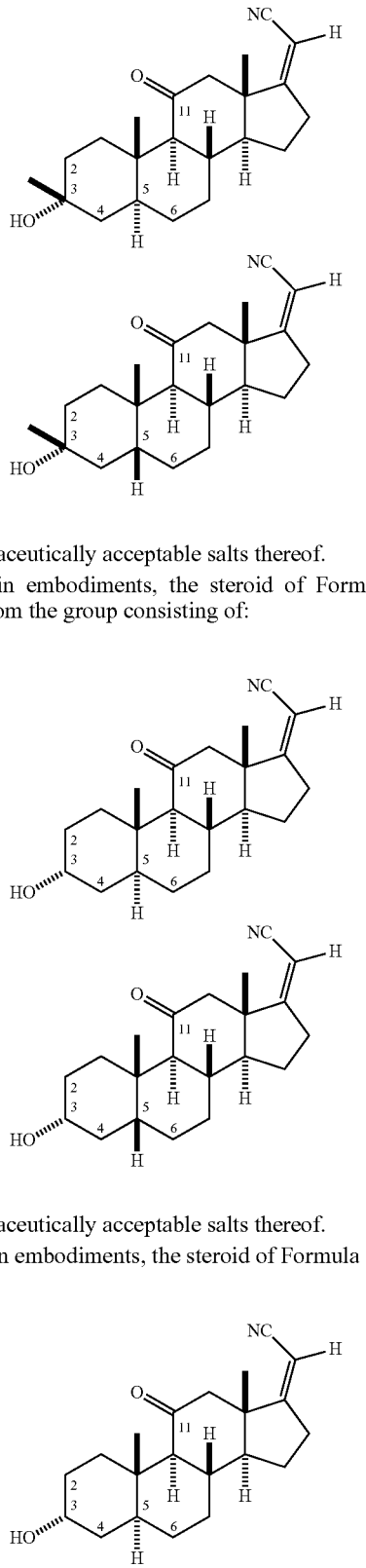

and pharmaceutically acceptable salts thereof.

In certain embodiments, the steroid of Formula (I) is selected from the group consisting of:

and pharmaceutically acceptable salts thereof.

In certain embodiments, the steroid of Formula (I) is:

or a pharmaceutically acceptable salt thereof.

In certain embodiments, the steroid of Formula (I) is selected from the group consisting of:

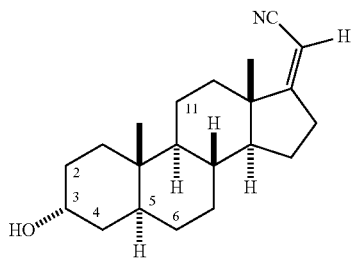

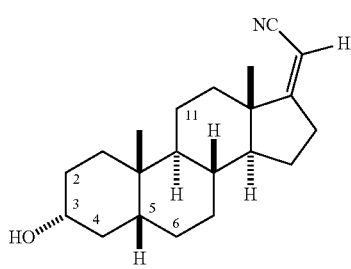

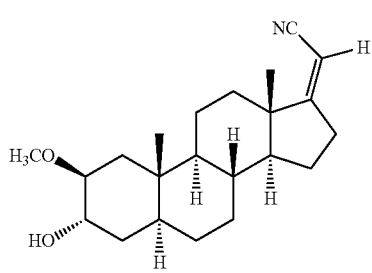

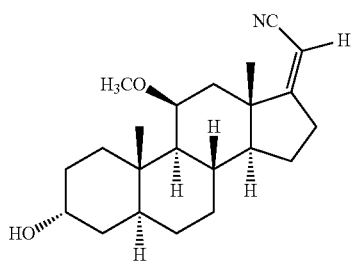

and pharmaceutically acceptable salts thereof.

In certain embodiments, the steroid of Formula (I) is selected from the group consisting of:

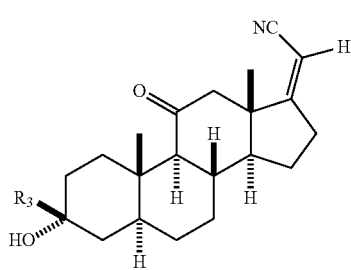

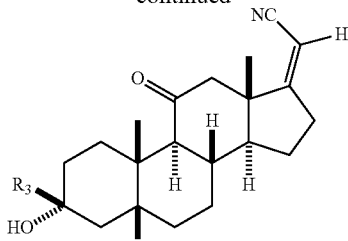

and pharmaceutically acceptable salts thereof, wherein $R_3$ is as defined herein. In certain embodiments, $R_3$ is selected from the group consisting of methyl and trifluoromethyl. In certain embodiments, $R_3$ is methyl. In certain embodiments, $R_3$ is trifluoromethyl.

In this regard it is to be noted that the structures provided above are of various exemplary embodiments. As such, they should not be viewed in a limiting sense.

2. Prodrug Structure

In another particular embodiment, the present disclosure is in general directed to prodrugs of the various steroids detailed above. Generally speaking, as used herein, a "prodrug" refers to an inactive, or significantly less active, form of the steroids detailed above (and in particular the steroids of Formula (I)), which after administration is metabolized in vivo into one or more active metabolites of the steroid of Formula (I). The prodrug may be formed using means generally known in the art, and therefore may take essentially any form that would be recognized to one of ordinary skill in the art. The prodrugs of the present disclosure may advantageously provide improved absorption, distribution, metabolism and/or excretion optimization, as well as improved oral bioavailability of the steroids detailed above (and in particular the steroids of Formula (I)).

In another particular embodiment of the present disclosure the prodrug of a steroid disclosed herein has a structure of Formula (II):

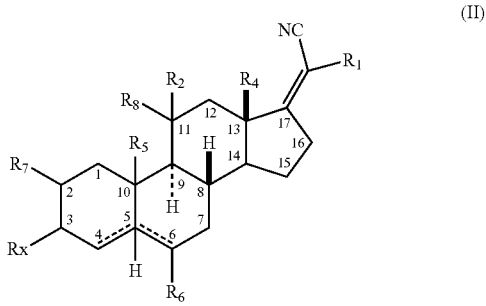

(II)

or a pharmaceutically acceptable salt thereof;
wherein:
$R_1$ is H;
$R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present;
$R_x$ is =O, OH, or $OR_d$, where $R_d$ is H or $C(O)R_e$, where $R_e$ is optionally substituted $C_1$-$C_{22}$ alkyl or optionally substituted $C_2$-$C_{22}$ alkenyl, with the proviso that when $R_x$ is OH, it is in the beta configuration;
$R_4$ and $R_5$ are each independently selected from H and unsubstituted $C_1$-$C_4$ alkyl;
$R_6$ is H, optionally substituted $C_1$-$C_4$ alkyl, or optionally substituted $C_1$-$C_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl; and,

- - - denotes an optional, additional C—C bond, resulting in either a C=C bond between $C_4$-$C_5$ or $C_5$-$C_6$, with the proviso that when present, the $C_5$—H substituent is not present.

In this regard, it is to be noted that the present disclosure contemplates and is intended to encompass all of the various combinations and permutations (i.e., combinations of substituent options, locations and stereochemical configurations) possible here.

As generally defined above, $R_x$ is =O, OH, or $OR_d$, where $R_d$ is H or $C(O)R_e$, where $R_e$ is optionally substituted $C_1$-$C_{22}$ alkyl or optionally substituted $C_2$-$C_{22}$ alkenyl (including for example optionally substituted $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl or $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkenyl), with the proviso that when $R_x$ is OH, it is in the beta (up) configuration. In certain embodiments, $R_x$ is =O. In certain embodiments, $R_x$ is OH in the beta (up) configuration. In certain embodiments, $R_x$ is $OR_d$, $R_d$ is $C(O)R_e$, and $R_e$ is optionally substituted $C_1$-$C_{22}$ alkyl or optionally substituted $C_2$-$C_{22}$ alkenyl, e.g., $C(O)CH_3$, and in such instances, the group Rx is provided in either the alpha or beta configuration. In certain embodiments, wherein $R_x$ is $OR_d$, and $R_d$ is H, then $R_x$ is OH in the beta (up) configuration.

As generally defined above, $R_2$ is =O, H, or $OR_a$, where $R_a$ is selected from H, optionally substituted $C_1$-$C_4$ alkyl, or optionally substituted aryl, with the proviso that when $R_2$ is =O, $R_8$ is not present. In certain embodiments, $R_2$ is =O and $R_8$ is not present. In certain embodiments, $R_2$ is H. In certain embodiments, $R_2$ is $OR_a$. In certain embodiments, $R_2$ is $OR_a$ and $R_a$ is optionally substituted $C_1$, $C_2$, $C_3$ or $C_4$ alkyl (e.g., methyl, ethyl), optionally substituted benzyl, or $C_1$, $C_2$, $C_3$ or $C_4$ alkyl substituted with O-aryl, such as O-benzyl. In certain embodiments, $R_2$ is $OR_a$ and $R_a$ is optionally substituted aryl. In certain embodiments, $R_2$ is $OR_a$ and $R_a$ is H.

As generally defined above, $R_4$ is H or unsubstituted $C_1$-$C_4$ alkyl. In certain embodiments, $R_4$ is H. In certain embodiments, $R_4$ is unsubstituted $C_1$, $C_2$, $C_3$ or $C_4$ alkyl (e.g., methyl, ethyl, n-propyl, isopropyl, or n-butyl).

As generally defined above, $R_5$ is H or unsubstituted $C_1$-$C_4$ alkyl. In certain embodiments, $R_5$ is H. In certain embodiments, $R_5$ is unsubstituted $C_1$, $C_2$, $C_3$ or $C_4$ alkyl (e.g., methyl, ethyl, n-propyl, isopropyl, or n-butyl). In certain embodiments, $R_5$ is in the beta (up) position.

As generally defined above, $R_6$ is H, optionally substituted $C_1$-$C_4$ alkyl, or optionally substituted $C_1$-$C_4$ alkoxy. In certain embodiments, $R_6$ is H. In certain embodiments, $R_6$ is optionally substituted $C_1$, $C_2$, $C_3$, or $C_4$ alkyl (e.g., methyl). In certain embodiments, $R_6$ is optionally substituted $C_1$, $C_2$, $C_3$ or $C_4$ alkoxy (e.g., methoxy, ethoxy, n-propyloxy, isopropyloxy, or n-butoxy). In certain embodiments, when $R_6$ is a non-hydrogen group, $R_6$ is in the alpha (down) position. In certain embodiments, when $R_6$ is a non-hydrogen group, $R_6$ is in the beta (up) position.

As generally defined above, $R_7$ is H, optionally substituted $C_1$-$C_4$ alkoxy, or an optionally substituted morpholinyl ring. In certain embodiments, $R_7$ is H. In certain embodiments, $R_7$ is optionally substituted $C_1$, $C_2$, $C_3$ or $C_4$ alkoxy (e.g., methoxy, ethoxy, n-propyloxy, isopropyloxy, or n-butoxy). In certain embodiments, $R_7$ is an optionally substituted morpholinyl ring. In certain embodiments, when $R_7$ is a non-hydrogen group, $R_7$ is in the alpha (down) position. In certain embodiments, when $R_7$ is a non-hydrogen group, $R_7$ is in the beta (up) position.

As generally defined above, $R_8$, when present, is H or optionally substituted $C_1$-$C_4$ alkyl. In certain embodiments, $R_8$ is H. In certain embodiments, $R_8$ is $C_1$, $C_2$, $C_3$ or $C_4$ optionally substituted alkyl (e.g., methyl). In certain embodiments, when $R_8$ is optionally substituted $C_1$-$C_4$ alkyl, $R_8$ is in the alpha (down) position. In certain embodiments when $R_8$ is optionally substituted $C_1$-$C_4$ alkyl, $R_8$ is in the beta (up) position.

In certain embodiments, $R_2$ and $R_8$ are both H. In certain embodiments, $R_2$ is $OR_a$ and $R_8$ is H.

As generally defined above, - - - denotes an optional, additional C—C bond, resulting in either a C=C bond between $C_4$-$C_5$ or $C_5$-$C_6$, with the proviso that when present, the $C_5$—H substituent is not present. In certain embodiments, the additional C—C bond is absent, and the hydrogen at $C_5$ is in the alpha or beta position. In certain embodiments, the additional C—C bond is absent, and the hydrogen at $C_5$ is in the alpha (down) position. In certain embodiments, the additional C—C bond is absent, and the hydrogen at $C_5$ is in the beta (up) position. In certain embodiments, - - - denotes an additional C—C bond, resulting in a C=C bond between $C_4$-$C_5$. In certain embodiments, - - - denotes an additional C—C bond, resulting in a C=C bond between $C_5$-$C_6$.

In certain embodiments, prodrugs of the present disclosure may be selected from among those encompassed by the structure of Formula (II), wherein $R_2$ is =O. In certain embodiments, $R_2$ is H and $R_8$ is H, e.g., $C_{11}$ thus having two hydrogen atoms bound thereto as substituents. In certain embodiments, $R_2$ may be $OR_a$, wherein $R_a$ is methyl, optionally substituted benzyl, or $C_1$-$C_4$ alkyl substituted with O-aryl, such as O-benzyl. In certain embodiments, $R_x$ is =O. In certain embodiments, $R_x$ is β-hydroxy. In certain embodiments, $R_x$ is $OR_d$, where $R_d$ is H or $C(O)R_e$, where $R_e$ is optionally substituted $C_1$-$C_4$ alkyl (e.g., methyl). In certain embodiments, each of $R_4$, $R_5$ and $R_6$ are independently selected from H and methyl. In certain embodiments, $R_5$ is in the beta-configuration. In certain embodiments, $R_6$ is optionally substituted alkyl, e.g., methyl, optionally in the alpha-configuration when the carbon-carbon double bond between $C_5$-$C_6$ is absent. In certain embodiments, $R_6$ is optionally substituted alkyl, e.g., methyl, optionally in the beta-configuration when the carbon-carbon double bond between $C_5$-$C_6$ is absent. In certain embodiments, $R_7$ is selected from H, methoxy, ethoxy, and an unsubstituted morpholinyl ring. In certain embodiments, $R_7$ is a non-hydrogen group, $R_7$ is in the β-position. In certain embodiments, a carbon-carbon double bond (or unsaturated bond) may be present between the $C_4$-$C_5$, or $C_5$-$C_6$, carbon atoms. In certain embodiments, $R_8$, when present, is selected from H or optionally substituted $C_1$-$C_4$ alkyl, preferably methyl and more preferably alpha-methyl.

In certain embodiments, $R_x$ is OH and in the beta position. In certain embodiments, a carbon-carbon double bond is present between the $C_4$-$C_5$ carbon atoms. In certain embodiments, a carbon-carbon double bond is present between the $C_5$-$C_6$ carbon atoms. In certain embodiments, $R_2$ is =O. In certain embodiments, $R_2$ is methoxy. In certain embodiments, $R_7$ is H. In certain embodiments, $R_7$ is β-methoxy. In certain embodiments, $R_7$ is β-ethoxy.

In certain embodiments, wherein $R_4$ is methyl, $R_5$ is methyl in the beta position, and $R_6$ is H, provided is a compound of Formula (II-a):

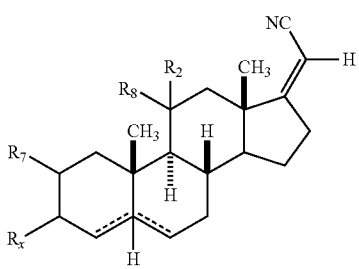

(II-a)

or a pharmaceutically acceptable salt thereof, wherein - - -, $R_x$, $R_2$, $R_7$ and $R_8$ are as defined herein. In certain embodiments, $R_x$ is =O. In certain embodiments, $R_x$ is OH in the beta (up) configuration. In certain embodiments, each instance of - - - is absent and $C_5$—H is in the alpha position. In certain embodiments, each instance of - - - is absent and $C_5$—H is in the beta position. In certain embodiments, - - - represents an additional C—C bond, resulting in either a C=C bond between $C_4$-$C_5$ or $C_5$-$C_6$.

In certain embodiments of Formula (II-a), wherein $R_2$ is =O and $R_8$ is absent, provided is a compound of Formula (II-b):

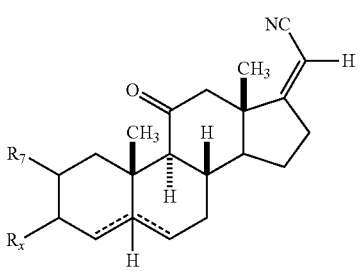

(II-b)

or a pharmaceutically acceptable salt thereof, wherein - - -, $R_x$, and $R_7$ are as defined herein. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II-a), wherein $R_2$ is H and $R_8$ is H, provided is a compound of Formula (II-c):

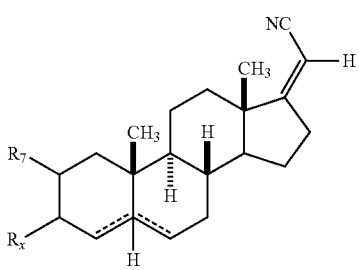

(II-c)

or a pharmaceutically acceptable salt thereof, wherein - - -, $R_x$, and $R_7$ are as defined herein. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II-a), wherein $R_2$ is $OR_a$ and $R_8$ is H, provided is a compound of Formula (II-d):

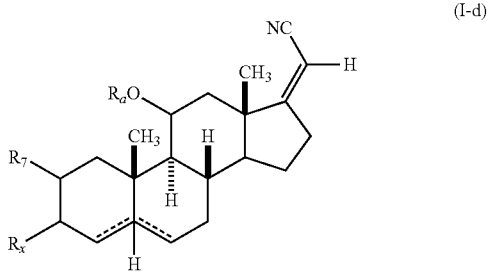

(I-d)

or a pharmaceutically acceptable salt thereof, wherein ———, $R_x$, $R_7$, and $R_a$ are as defined herein. In certain embodiments, $R_x$ is =O. In certain embodiments, $R_x$ is OH in the beta (up) configuration. In certain embodiments, each instance of - - - is absent $C_5$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II-a), wherein $R_7$ is H, provided is a compound of Formula (II-e):

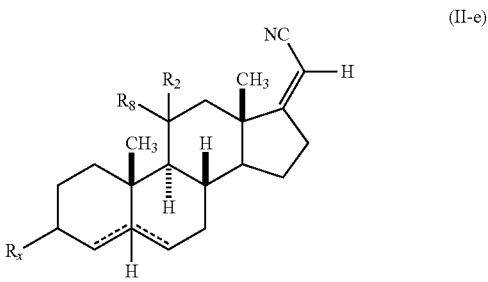

(II-e)

or a pharmaceutically acceptable salt thereof, wherein - - -, $R_x$, $R_2$ and $R_8$ are as defined herein. In certain embodiments, $R_x$ is =O. In certain embodiments, $R_x$ is OH in the beta (up) configuration. In certain embodiments, each instance of - - - is absent $C_8$—H is in the alpha position. In certain embodiments, each instance of - - - is absent $C_5$—H is in the beta position. In certain embodiments, - - - represents an additional C—C bond, resulting in either a C=C bond between $C_4$-$C_5$ or $C_5$-$C_6$.

In certain embodiments of Formula (II-a), wherein each instance of - - - is absent $C_5$—H is in the alpha position, provided is a compound of Formula (II-f):

(II-f)

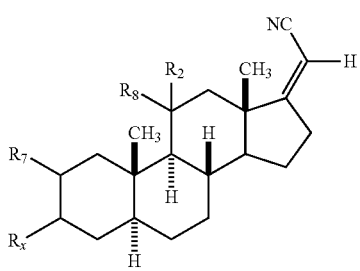

or a pharmaceutically acceptable salt thereof, wherein $R_x$, $R_2$, $R_7$ and $R_8$ are as defined herein. In certain embodiments, $R_x$ is =O. In certain embodiments, $R_x$ is OH in the beta (up) configuration.

In certain embodiments of Formula (II-f), wherein $R_7$ is H, provided is a compound of Formula (II-g):

(II-g)

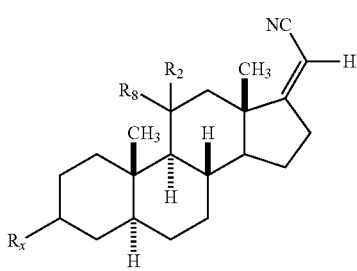

or a pharmaceutically acceptable salt thereof, wherein $R_x$, $R_2$ and $R_8$ are as defined herein. In certain embodiments, $R_x$ is =O. In certain embodiments, $R_x$ is OH in the beta (up) configuration.

In certain embodiments of Formula (II-f), wherein $R_2$ is =O, provided is a compound of Formula (II-h):

(II-h)

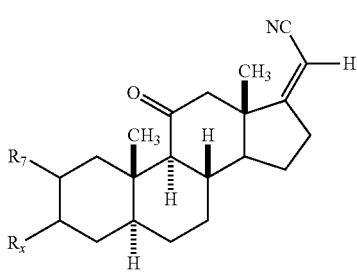

or a pharmaceutically acceptable salt thereof, wherein $R_x$ and $R_7$ are as defined herein. In certain embodiments, $R_x$ is =O. In certain embodiments, $R_x$ is OH in the beta (up) configuration.

In certain embodiments of Formula (II-f), wherein $R_2$ is $OR_a$, provided is a compound of Formula (II-i):

(II-i)

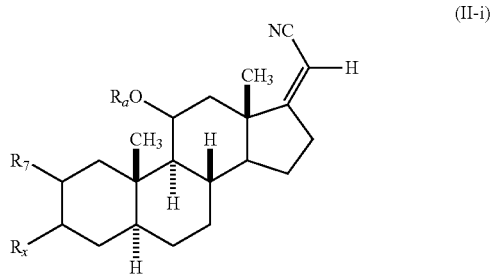

or a pharmaceutically acceptable salt thereof, wherein $R_x$, $R_a$, and $R_7$ are as defined herein. In certain embodiments, $R_x$ is =O. In certain embodiments, $R_x$ is OH in the beta (up) configuration.

In certain embodiments of Formula (II-a), wherein - - - represents an additional C—C bond, resulting in a C=C bond between $C_4$-$C_5$ provided is a compound of Formula (II-j):

(II-j)

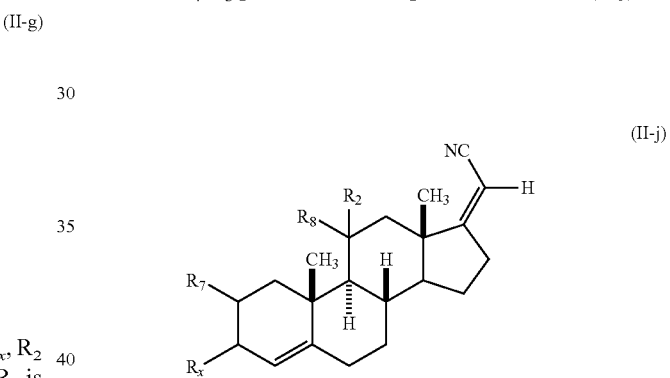

or a pharmaceutically acceptable salt thereof, wherein $R_x$, $R_2$, $R_7$ and $R_8$ are as defined herein. In certain embodiments, $R_x$ is =O. In certain embodiments, $R_x$ is OH in the beta (up) configuration.

In certain embodiments of Formula (II-a), wherein - - - represents an additional C—C bond, resulting in a C=C bond between $C_5$-$C_6$ provided is a compound of Formula (II-k):

(II-k)

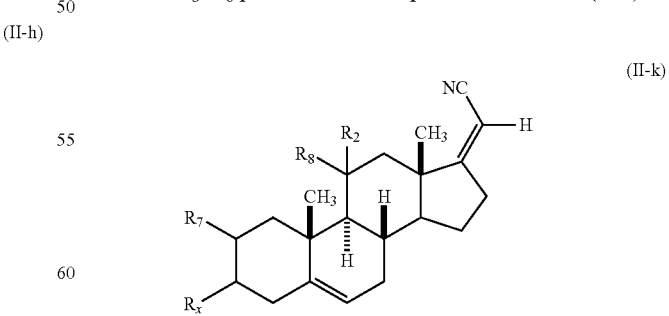

or a pharmaceutically acceptable salt thereof, wherein $R_x$, $R_2$, $R_7$ and $R_8$ are as defined herein. In certain embodiments, $R_x$ is =O. In certain embodiments, $R_x$ is OH in the beta (up) configuration.

Exemplary compounds of Formula (II) include, when $R_x$ is beta —$OR_d$, include but are not limited to:
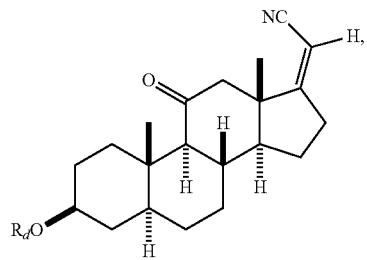
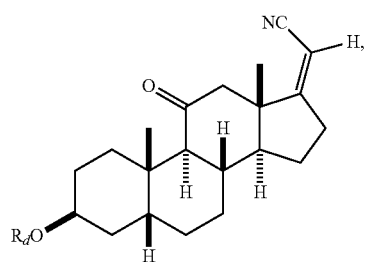
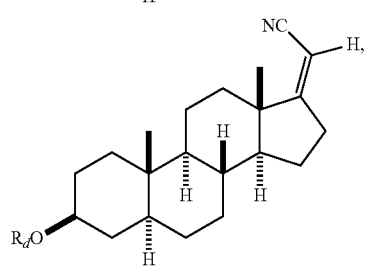
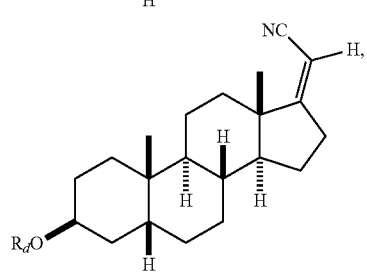
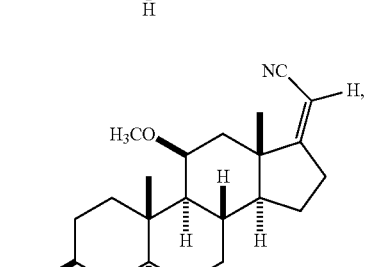
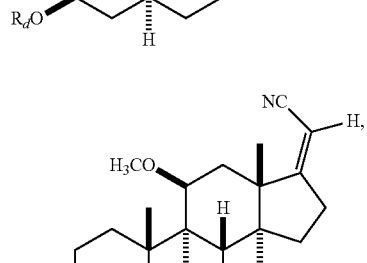
-continued
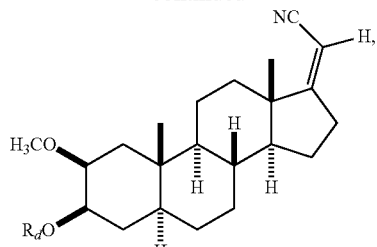
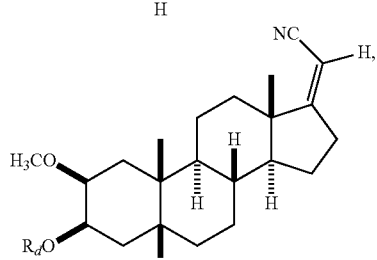
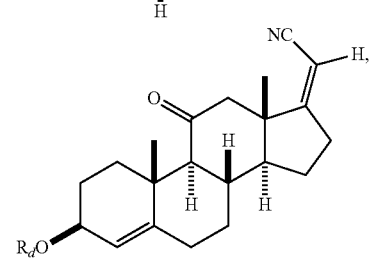
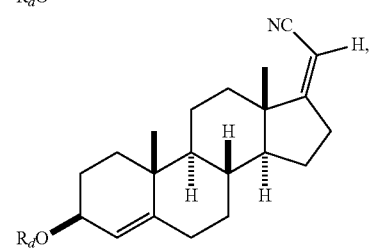
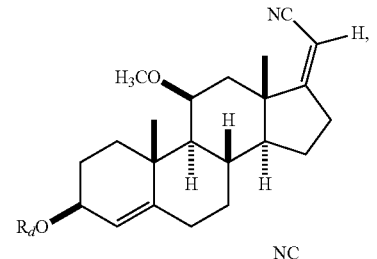
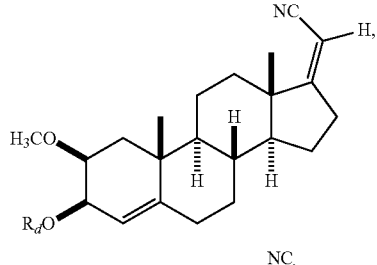
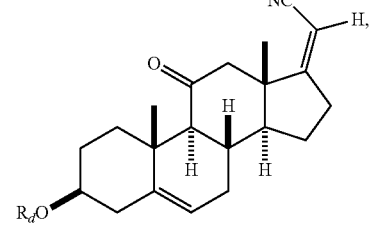

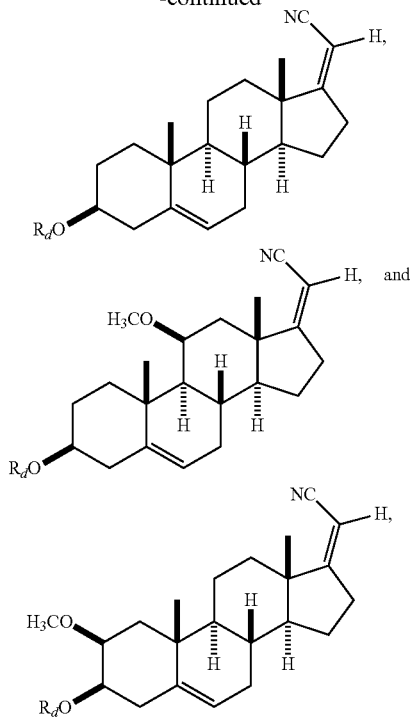
and pharmaceutically acceptable salts thereof, wherein $R_d$ is H or $C(O)R_e$. In certain embodiments, $R_d$ is H. In certain embodiments, $R_d$ is $C(O)R_e$, e.g., —$C(O)CH_3$.
Exemplary compounds of Formula (II) include, when $R_x$ is =O, include but are not limited to:
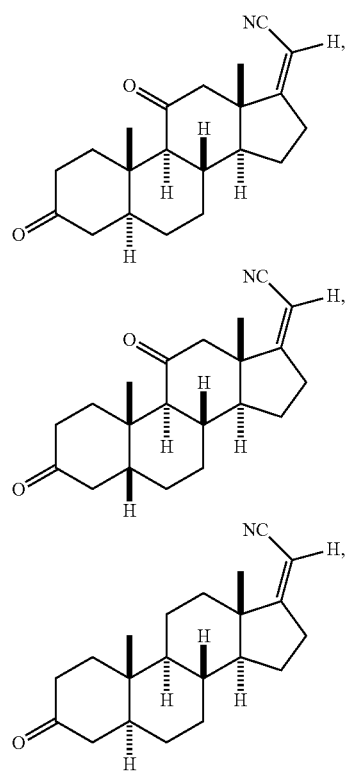
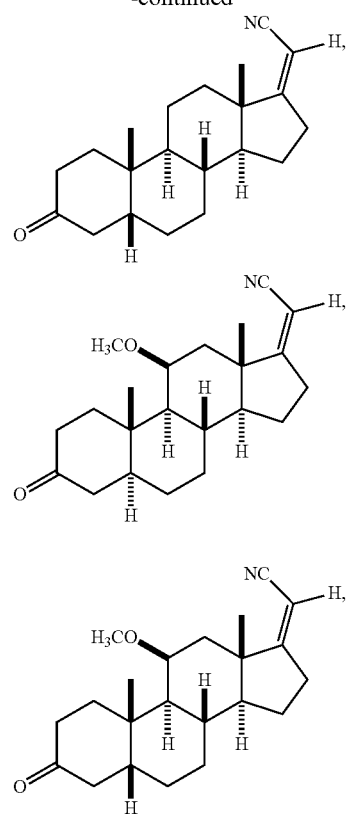
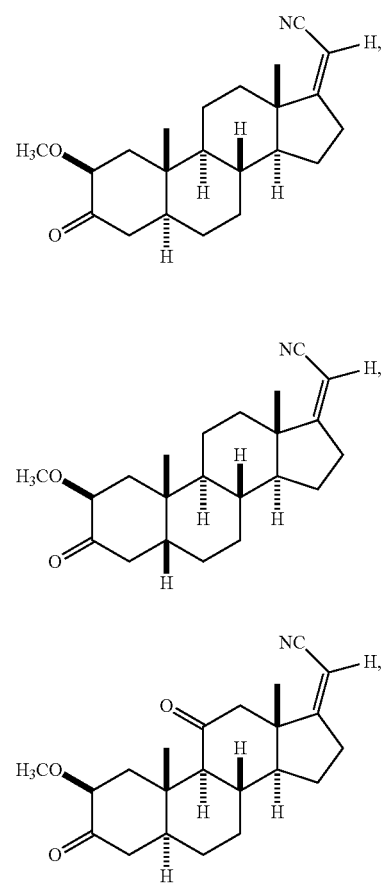

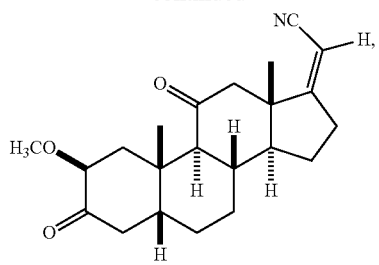
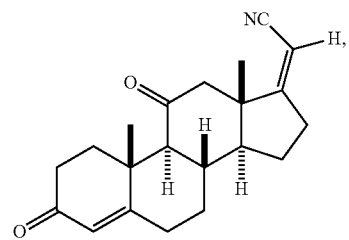
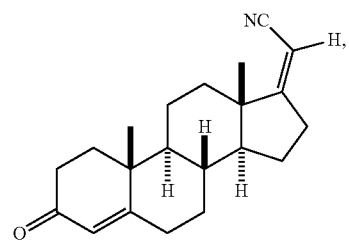
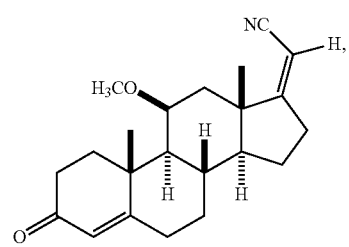
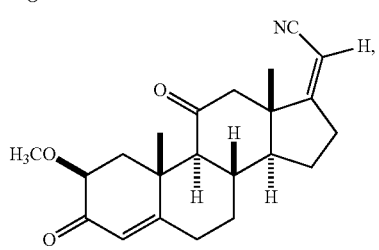
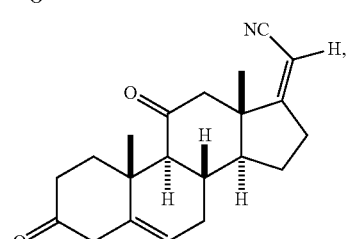
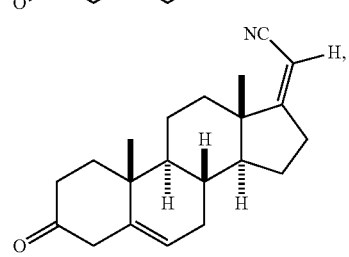
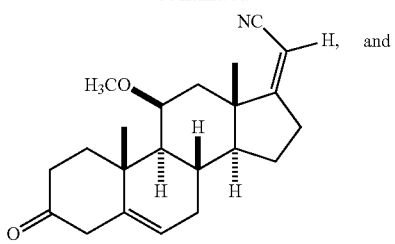
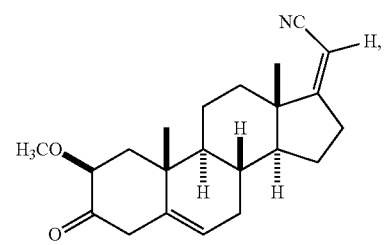
and pharmaceutically acceptable salts thereof.
In certain embodiments, the compound of Formula (II) is selected from the group consisting of:
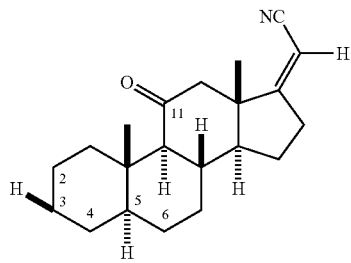
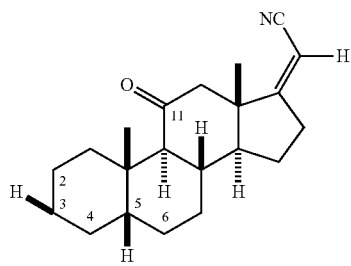
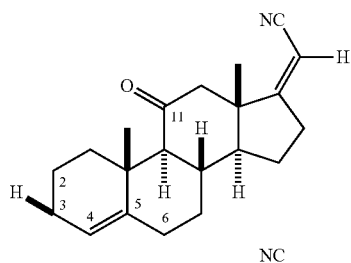
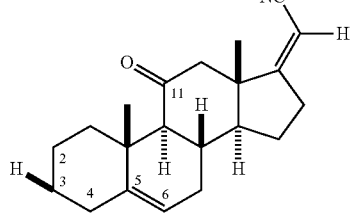
and pharmaceutically acceptable salts thereof.

In certain embodiments, the compound of Formula (II) is selected from the group consisting of:

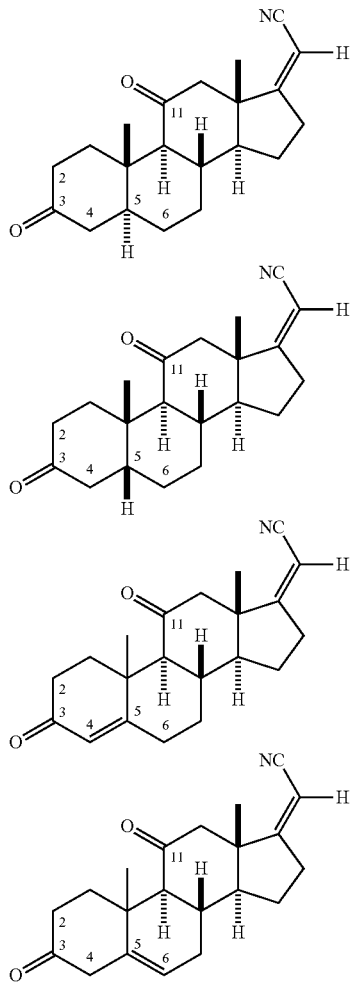

and pharmaceutically acceptable salts thereof.

In this regard it is to be noted that the structures provided above are of various exemplary embodiments. As such, they should not be viewed in a limiting sense.

3. Methods of Preparation and Pharmaceutical Compositions

It is to be noted that the compounds or steroids of the present disclosure, or the prodrugs thereof, may in various embodiments be prepared or used in accordance with means generally known in the art. For example, in certain embodiments, the steroids or prodrugs of the present disclosure may be prepared or used in a pharmaceutically acceptable salt form, for example, where $R_7$ is an optionally substituted morpholinyl ring. Suitable salt forms include, for example, citrate or chloride salt forms.

In various embodiments of the present disclosure, a pharmaceutical composition is disclosed that may comprise a steroid, a prodrug, or a combination of two or more thereof in accordance with the formulas of the present disclosure. The compounds or steroids of the present disclosure (or the prodrugs thereof), as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or steroids of the present disclosure are useful for potentiating GABA at $GABA_A$ receptors thereby inducing anesthesia or treating disorders related to GABA function (e.g., insomnia, mood disorders, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted steroids, or prodrugs, or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted steroids, or prodrugs, or pharmaceutically acceptable salts thereof, or a pharmaceutical composition thereof. In certain embodiments, the disorder is selected from the group consisting of insomnia, mood disorders, convulsive disorders, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or steroids of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The compounds, steroids, and prodrugs of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.,) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to effect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the invention are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

4. Definitions

The term "steroid" as used herein describes an organic compound containing in its chemical nucleus the cyclopenta [α]phenanthrene ring system.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "prodrug" as used herein describes a pharmacological substance that is administered in a less active or inactive form. After administration, a prodrug is metabolized in vivo e.g., via hydrolysis, oxidation, or reaction under biological conditions (in vitro or in vivo), to provide an active metabolite. See, e.g., Wu, *Pharmaceuticals* (2009) 2:77-81. In certain embodiments, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract or the skin, or it may enhance drug stability for long-term storage.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the subject is a human.

As used herein, a "therapeutically effective amount" "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "$C_{1-4}$ alkyl" is intended to encompass, $C_1$, $C_2$, $C_3$, $C_4$, $C_{1-3}$, $C_{1-2}$, $C_{2-4}$, $C_{2-3}$ and $C_{3-4}$ alkyl, while "$C_{1-22}$ alkyl" is intended to encompass, for example, $C_1$, $C_2$, $C_3$, $C_4$, etc., as well as $C_{1-21}$, $C_{1-20}$, $C_{1-15}$, $C_{1-10}$, $C_{2-20}$, $C_{2-15}$, $C_{2-10}$, $C_{3-15}$, $C_{3-10}$, etc. alkyl.

As used herein, "alkyl" refers to a radical of a straight-chain or branched saturated hydrocarbon group having from, in some embodiments, 1 to 4 carbon atoms ("$C_{1-4}$ alkyl"), and in other embodiments 1 to 22 carbon atoms ("$C_{1-22}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 4 carbon atom ("$C_{2-4}$ alkyl"). In yet other embodiments, an alkyl group has 1 to 21 carbon atoms ("$C_{1-21}$ alkyl"), 1 to 20 carbon atoms ("$C_{1-20}$ alkyl"), 1 to 15 carbon atoms ("$C_{1-15}$ alkyl"), 1 to 10 carbon atoms ("$C_{1-10}$ alkyl"), etc. Examples of such alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), pentyl ($C_5$), and the like.

As used herein, "alkenyl" or "alkene" refers to a radical of a straight-chain or branched hydrocarbon group having from, in some embodiments, 2 to 4 carbon atoms ("$C_{2-4}$ alkenyl"), and in other embodiments 2 to 22 carbon atoms ("$C_{2-22}$ alkenyl"), and one or more carbon-carbon double bonds. In some embodiments, an alkenyl group has 2 to 3 carbon atoms ("$C_{2-3}$ alkenyl"). In some embodiments, an alkenyl group has 2 carbon atoms ("$C_2$ alkenyl"). In yet other embodiments, an alkenyl group has 2 to 21 carbon atoms ("$C_{2-21}$ alkenyl"), 2 to 20 carbon atoms ("$C_{2-20}$ alkenyl"), 2 to 15 carbon atoms ("$C_{2-15}$ alkenyl"), 2 to 10 carbon atoms ("$C_{2-10}$ alkyl"), etc. The one or more carbon-carbon double bonds can be internal (such as in 2-butenyl) or terminal (such as in 1-butenyl). Examples of such alkenyl groups include ethenyl ($C_2$), 1-propenyl (C3), 2-propenyl ($C_3$), 1-butenyl ($C_4$), 2-butenyl ($C_4$), butadienyl ($C_4$), 1-pentenyl ($C_5$), 2-pentenyl ($C_5$), and the like.

As used herein, "alkynyl" or "alkyne" refers to a radical of a straight-chain or branched hydrocarbon group having from 2 to 4 carbon atoms and one or more carbon-carbon triple bonds ("$C_{2-10}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl (C3), 1-butynyl ($C_4$), 2-butynyl ($C_4$), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Example.

Compound Chemistry

In accordance with the following methods and Examples, the following compounds were prepared:

Chart 1

1
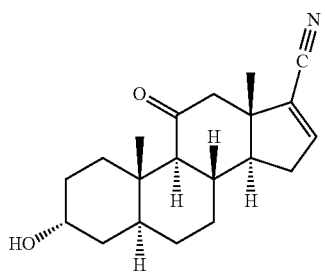

2
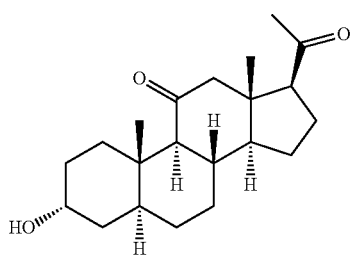

3
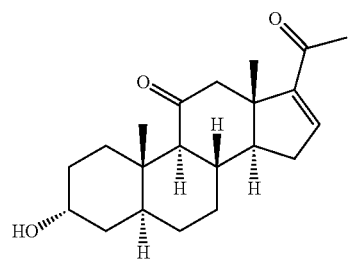

-continued

4
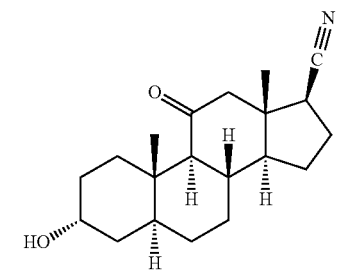

Chart 2

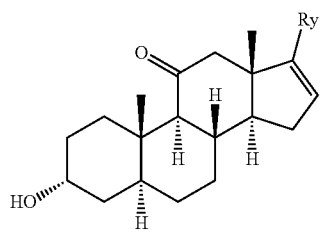

5a: Δ$^{16}$; Ry = CHO
5b: Ry = 17β-CHO
5c: Ry = 17β-CH$_2$CN

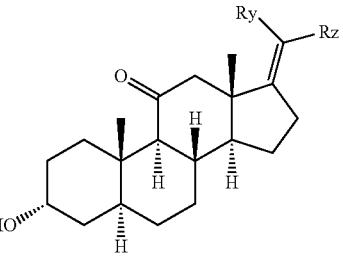

6a: Ry = CN; Rz = H
6b: Ry = H; Rz = CN
6c: Ry = CN; Rz = CH$_3$
6d: Ry = CH$_3$; Rz = CN

Compounds 1-4 were prepared using methods known in the art (see Bandyopadhyaya, A. K., et al., "Neurosteroid analogues. 15. A comparative study of the anesthetic and GABAergic actions of alphaxalone, Δ$^{16}$-alphaxalone and their corresponding 17-carbonitrile analogues. Bioorg. Med. Chem. Lett., 20: 6680-4 (2010)). Compound 8 was prepared from adrenosterone (Compound 7) as described in Bandyopadhyaya, et al. by Scheme 1$^a$:

Reduction of the carbonitrile group of compound 8 with DIBALH reduced the C-11 carbonyl group. This diol intermediate was not characterized but was instead oxidized using PCC to intermediate Compound 9 in an overall yield of about 48% for the two-step procedure. Removal of the MOM protecting group produced Compound 5a at about an 85% yield. Hydrogenation of compound 5a using a Lindlar's catalyst produced Compound 5b at about a 70% yield.

Next, Compound 6a (about a 25% yield) and Compound 6b (about a 44% yield) were prepared as an isomeric mixture from Compound 7 by a Wittig-Horner reaction and subsequently separated by preparative thin layer chromatography (TLC) (Scheme 2$^a$).

The Z stereochemistry for the carbonitrile substituent (i.e., the vinyl cyano group) on Compound 6a was established by the crystal structure determination displayed in FIG. 1. Hydrogenation of Compound 6b produced Compound 5c at about a 57% yield.

Alphaxalone (compound 1) was used as a starting material to prepare additional $\Delta^{17(20)}$ analogues through the process of Scheme 3:

Compound 1 was acetylated to yield Compound 10 and Compound 10 was then used to prepare alpha-cyanohydrin diastereomers (Compound 11) following a procedure known in the art for preparing similar compounds from other 20-ketosteroid precursors (see Sarett, L. H., *A new method for the preparation of 17(alpha)-hydroxy-20-ketopregnanes*. J. Am. Chem. Soc., 70: 1454-8 (1948)). After verification through nuclear magnetic resonance (NMR) that intermediate Compound 11 was formed, Compound 11 was immediately subjected to a dehydration reaction to yield)$\Delta^{17(20)}$ Compounds 12a and 12b. Purification by recrystallizations and column chromatography yielded pure Compound 12a (about 5.2%) and pure Compound 12b (about 21%). Saponification of the 3-alpha-acetoxy groups of Compounds 12a and 12b produced the desired analogues (Compounds 6c (about 82% yield) and 6d (about 82% yield)), respectively.

Comparison of the $^1$H NMR spectra of Compounds 6a and 6b showed that the C-18 methyl group in Compound 6a was shifted downfield relative to the C-18 methyl group of Compound 6b due to a deshielding effect of the nearby nitrile group. Accordingly, because the C-18 methyl group of Compound 6c was shifted downfield relative to that found for the C-18 methyl group of Compound 6d, Compound 6c was determined by this spectroscopic difference to be the Z double bond isomer.

As further illustrated in the Schemes below, other steroid compounds were prepared by a Wittig-Horner reaction (similar to Compounds 6(a) and 6(b) as shown in Scheme $2^a$). Notably, both Z and E vinylcyano isomers were produced in the reactions. These isomers were subsequently separated by various means known in the art (and/or as further illustrated in Examples that follow). Specifically, Compounds 13-17 were prepared through the processes of Scheme 4-8, below.

General Methods

The compounds discussed in the present disclosure were produced as discussed elsewhere throughout this disclosure and by the following methods.

Solvents were either used as purchased or dried and purified by standard methodology. Extraction solvents were dried with anhydrous $Na_2SO_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in $CDCl_3$ at ambient temperature at 300 MHz ($^1$H) or 74 MHz ($^{13}$C). Purity was determined by TLC on 250 μm thick Uniplates™ from Analtech (Newark, Del.). All pure compounds (purity >95%) gave a single spot on TLC. Elemental analyses were performed by M-H-W Laboratories (Phoenix, Ariz.). Compounds 1 and 7 were purchased from Steraloids (Newport, R.I.). Compounds 2, 3 and 4 were prepared as described in Bandyopadhyaya, et al. (Bioorg. Med. Chem. Lett., 20: 6680-4 (2010)).

(3α,5α)-3-Hydroxy-11-oxoandrost-16-ene-17-carboxaldehyde (Compound 5a). Compound 9 (110 mg, 0.31 mmol) dissolved in EtOH (8 mL) and 6 N HCl (2 mL) was stirred at room temperature for about 6 h. The reaction was adjusted to basic pH by adding aqueous $NaHCO_3$ and solvents were removed under reduced pressure to give a residue. Water was added and the product was isolated by extraction with $CH_2Cl_2$. The combined extracts were dried and concentrated to give a white solid, which was purified by passing through a short column of silica gel (eluted with 50% EtOAc in hexanes) to give compound 5a as a white solid (83 mg, 85%): mp 164-167° C.; $[\alpha]_D^{20}$=+71.2 (c=0.11, $CHCl_3$); IR $v_{max}$ 3392, 2922, 1702, 1677 cm$^{-1}$; $^1$H NMR δ 9.70 (s, 1H), 6.85 (br s, 1H), 4.05 (br s, 1H), 2.98 (d, 1H, J=12.6 Hz), 2.44 (d, 1H, J=12.6 Hz), 1.02 (s, 3H), 0.84 (s, 3H); $^{13}$C NMR δ 209.6, 189.1, 154.6, 152.3, 66.2, 66.0, 56.2, 53.6, 47.5, 39.1, 36.1, 35.3, 35.2, 32.4, 32.1, 30.9, 28.9, 27.8, 17.3, 10.9. Anal. Calcd for $C_{20}H_{28}O_3$: C, 75.91%; H, 8.92%. Found: C, 75.73%; H, 9.04%.

(3α,5α,17β)-3-Hydroxy-11-oxoandrostane-17-carboxaldehyde (Compound 5b). A mixture of the unsaturated aldehyde compound 5a (31 mg, 0.1 mmol), Lindlar's catalyst (60 mg) and EtOAc (10 mL) was hydrogenated in a Parr hydrogenation apparatus ($H_2$, 60 psi) for 4 h. The reaction mixture was then passed through a short silica gel column eluted with EtOAc. After solvent removal, the product was isolated as a solidified foam with a low melting point. Compound 5b (26 mg, 70%) had: $[\alpha]_D^{20}$=+61.9 (c=0.11, $CHCl_3$); IR $v_{max}$ 3391, 2921, 1706 cm$^{-1}$; $^1$H NMR δ 9.71 (d, 1H, J=1.9 Hz), 4.05 (b s, 1H), 1.01 (s, 3H), 0.71 (s, 3H); $^{13}$C NMR δ 209.5, 203.2, 66.2, 64.3, 61.1, 56.1, 55.5, 47.8, 38.9, 36.3, 35.8, 35.2, 32.6, 30.8, 28.8, 27.8, 24.1, 21.5, 14.6, 10.9. Anal. Calcd for $C_{20}H_{30}O_3$: C, 75.43%; H, 9.50%. Found: C, 75.21%; H, 9.73%.

(3α,5α)-3-Hydroxy-11-oxopregnan-21-carbonitrile (Compound 5c). A solution of compound 6c (90 mg, 10.3 mmol) in EtOAc (45 mL) and EtOH was hydrogenated in the presence of Pd/C (10%, 10 mg) overnight at 60 psi. The next day additional Pd/C (10 mg) was added and the hydrogenation was continued for an additional 12 h. The catalyst was removed by filtration through a short column of silica gel eluted with $CH_2Cl_2$ and the solvent was removed to yield a white solid. Crystallization from $Et_2O$/EtOAc/hexanes afforded compound 5c (52 mg, 57%): mp 176-178° C.; $[\alpha]_D^{20}$=+24.1 (c=0.25, $CHCl_3$); IR $v_{max}$ 3400, 2922, 2249, 1703 cm$^{-1}$; $^1$H NMR δ 4.03 (1H, m), 1.00 (3H, s), 0.58 (3H, s); $^{13}$C NMR δ 209.9, 119.2, 66.4, 64.5, 55.4, 54.9, 46.5, 45.8, 39.1, 37.2, 35.9, 35.4, 32.7, 31.0, 29.0, 28.6, 27.9, 23.9, 17.7, 13.2, 11.1. Anal. Calcd for $C_{21}H_{31}NO_2$: C, 76.55%; H, 9.48%; N, 4.25%. Found. C, 76.37%; H, 9.36%; N, 4.01%.

[3α,5α,17(20)Z]-3-Hydroxy-11-oxopregn-17(20)-ene-2'-nitrile (Compound 6a) and [3α,5α,17(20)E]-3-Hydroxy-11-oxopregn-17(20)-ene-2'-nitrile (Compound 6b). To a suspension of NaH (60% dispersion in oil, 0.55 mmol, 14 mg) in dry THF (5 mL) at 0° C. under $N_2$, diethyl(cyanomethyl)phosphonate (0.6 mmol, 0.1 mL) was added dropwise. After disappearance of the sodium hydride, compound 7 (147 mg, 0.48 mmol) in dry THF (10 mL) was added dropwise. This mixture was allowed to attain room temperature and stirred overnight. The reaction mixture was then poured into an aqueous solution of $NH_4Cl$ and the product was extracted with EtOAc. The combined extracts were washed with brine and dried. After solvent evaporation, the residue was purified on preparative TLC (4 plates) developed with EtOAc/hexanes (1:1) to obtain compound 6b (65 mg) and an unseparated mixture of compound 6a and unreacted compound 7 (56 mg). The latter mixture was again treated as just described with NaH (7 mg, 60% dispersion in oil, 0.17 mmol) and diethyl(cyanomethyl)phosphonate (0.03 mmol, 0.2 mL) to convert the unreacted compound 7 in the mixture to compounds 6a and 6b. Purification by preparative TLC provided the separable compounds 6a (40 mg) and 6b (5 mg).

Compound 6a (40 mg, 25%) had: mp 219-221° C. ($Et_2O$/hexanes), $[\alpha]_D^{20}$=+10.0 (c=0.18, $CHCl_3$); IR $v_{max}$ 3391, 2922, 2215, 1704, 1636 cm$^{-1}$; $^1$H NMR δ 5.15 (1H, t, J=2.4 Hz), 4.02 (1H, br s), 3.16 (1H, d, J=12 Hz), 0.99 (3H, s), 0.89 (3H, s); 13C NMR δ 208.7, 175.7, 115.8, 89.4, 66.3, 64.6, 54.6, 53.3, 49.6, 39.0, 35.9, 35.7, 35.4, 32.7, 32.5, 30.9, 29.0, 27.8, 23.5, 18.2, 11.1. Anal. Calcd for $C_{21}H_{29}NO_2$: C, 77.02%; H, 8.93%; N, 4.28%. Found. C, 77.17%; H, 9.13%; N, 4.26%.

Compound 6b (70 mg, 44%) had: mp 166-168° C. (Et$_2$O/hexanes), $[α]_D^{20}$=−5.9 (c=0.36, CHCl$_3$); IR ν$_{max}$ 3435, 2923, 2217, 1705, 1638 cm$^{-1}$; $^1$H NMR δ 4.95 (1H, t, J=2.7 Hz), 4.02 (1H, br s), 2.71-2.83 (2H, m), 0.99 (3H, s), 0.79 (3H, s); $^{13}$C NMR δ 208.6, 177.7, 116.8, 89.2, 66.2, 64.7, 53.5, 53.2, 49.5, 39.0, 36.2, 36.0, 35.4, 32.5, 30.9, 30.7, 28.9, 27.8, 23.6, 19.2, 11.1. Anal. Calcd for $C_{21}H_{29}NO_2$: C, 77.02%; H, 8.93%; N, 4.28%. Found. C, 76.91%; H, 8.86%; N, 4.21%.

[3α,5α,17(20)Z]-3-Hydroxy-11-oxopregn-17(20)-ene-20-carbonitrile (Compound 6c). Compound 12a (20 mg, 0.053 mmol) and K$_2$CO$_3$ (25 mg) in MeOH (3 mL) were refluxed for 2 h. After cooling to room temperature, the MeOH was removed under reduced pressure to give a residue. Water (25 mL) was added and the product was extracted with CH$_2$Cl$_2$. Solvent removal gave a solid which was purified by column chromatography on silica gel (eluted with 50% EtOAc in hexanes) to give the Compound 6c (15 mg, 82%): mp 203-205° C.; $[α]_D^{20}$=+4.0 (c=0.08, CHCl$_3$); IR ν$_{max}$ 3368, 2923, 2210, 1704, 1594, 1453 cm$^{-1}$; $^1$H NMR δ 4.05 (br s, 1H), 3.26 (d, 1H, J=12.4 Hz), 2.60-2.20 (m, 4H), 1.83 (br s, 3H), 1.01 (s, 3H), 0.88 (s. 3H); $^{13}$C NMR δ 208.9, 167.2, 118.5, 98.2, 66.2, 64.6, 54.9, 53.5, 49.0, 38.9, 35.8, 35.5, 35.2, 32.5, 31.1, 30.8, 28.9, 27.7, 23.2, 18.2, 18.0, 10.9. Anal. Calcd for $C_{22}H_{31}NO_2$: C, 77.38%; H, 9.15%; N, 4.10. Found: C, 77.19%; H, 9.14%, N, 3.86%.

[3α,5α,17(20)E]-3-(Acetyloxy)-11-oxopregn-17(20)-ene-20-carbonitrile (Compound 6d). Compound 12b (60 mg, 0.053 mmol) was converted into compound 6d using the procedure reported for the preparation of Compound 6c. Compound 6d (45 mg, 82%) had: mp 186-188° C.; $[α]_D^{20}$=−7.8 (c=0.18, CHCl$_3$); IR ν$_{max}$ 3468, 2924, 2210, 1704, 1639 cm$^{-1}$; $^1$H NMR δ 4.02 (br s, 1H), 2.76 (d, 1H, J=12.1 Hz), 2.69 (m, 2H), 2.56 (d, 1H, J=12.4 Hz), 2.09 (m, 1H), 1.85 (t, 3H, J=2 Hz), 0.98 (s, 3H), 0.84 (s, 3H); $^{13}$C NMR δ 209.1, 166.8, 119.6, 100.5, 66.0, 64.5, 55.1, 54.7, 49.2, 38.7, 35.7, 35.2, 33.2, 32.2, 30.7, 28.7, 27.6, 23.6, 17.0, 15.0, 10.8. Anal. Calcd for $C_{22}H_{31}NO_2$: C, 77.38%; H, 9.15%; N, 4.10. Found: C, 77.52%; H, 9.24%, N, 4.01%.

(3α,5α)-3-(Methoxymethoxy)-11-oxoandrost-16-ene-17-carboxaldehyde (Compound 9). To a cold (−78° C.) solution of Compound 8 (250 mg, 0.7 mmol) in CH$_2$Cl$_2$ was added 1 M DIBALH in toluene (2.1 mL, 2.1 mmol) and the reaction was stirred at −78° C. for 90 min. The excess DIBALH was quenched by adding few drops of acetone and then 1 M HCl (15 mL), and the cooling bath was removed. The biphasic mixture was stirred at room temperature for 0.5 h. The CH$_2$Cl$_2$ layer was separated and the aqueous phase was extracted with CH$_2$Cl$_2$. The combined CH$_2$Cl$_2$ extracts were washed with brine, dried and concentrated to give a pale yellow oil. This material was subjected to oxidation without any purification or characterization.

The pale yellow oil dissolved in CH$_2$Cl$_2$ (10 mL) and PCC (862 mg, 4 mmol) was stirred at room temperature for 3 h and the brown solution was purified by column chromatography (silica gel, eluted with 30% EtOAc in hexanes) to give Compound 9 (120 mg, 48%): mp 111-114° C.; IR ν$_{max}$ 2923, 1704, 1681, 1594, cm$^{-1}$; $^1$H NMR δ 9.69 (s, 1H), 6.85 (b s, 1H), 4.66 (d, 1H, J=6.8 Hz), 4.63 (d, 1H, J=6.9 Hz), 3.82 (s, 1H), 3.36 (s, 3H), 2.97 (d, 1H, J=12.6 Hz), 2.43 (d, 1H, J=6.6 Hz), 1.03 (s, 3H), 0.83 (s, 3H); $^{13}$C NMR δ 209.6, 189.1, 154.6, 152.3, 94.6, 71.4, 66.0, 56.3, 55.1, 53.6, 47.5, 39.8, 35.9, 35.2, 33.4, 32.4, 32.1, 31.6, 27.8, 26.0, 17.3, 11.1. Anal. Calcd for $C_{22}H_{32}O_4$: C, 73.30%; H, 8.95%. Found: C, 73.10%; H, 8.74%.

[3α,5α,17(20)Z]-3-(Acetyloxy)-11-oxopregn-17(20)-ene-20-carbonitrile (Compound 12a) and [3α,5α,17(20)E]-3-(Acetyloxy)-11-oxopregn-17(20)-ene-20-carbonitrile (Compound 12b). The acetylated steroid Compound 10 was prepared from compound 1 using a standard acetylation procedure (pyridine/AcOAc). Compound 10 (281 mg, 0.75 mmol), KCN (325 mg, 5 mmol), AcOH (0.8 mL), EtOH (3 mL) and water (0.2 mL) were stirred at 0° C. for 0.5 h and then allowed to warm to room temperature. Stirring was continued at room temperature for another 60 h. Water (50 mL) was added to the reaction mixture and the resulting white precipitate was filtered. The filter-cake was dried under high vacuum for 6 h. The NMR spectrum of this white solid showed that it was a mixture of diastereomeric cyanohydrins compound 11 and unreacted starting material. The product mixture was used without purification or further characterization.

The crude product mixture was dissolved in pyridine (3 mL) and POCl$_3$ (0.8 mL) was added at room temperature and the reaction was stirred for 15 hours. It was then cooled to 0° C. and carefully quenched with water and the biphasic solution was extracted with CH$_2$Cl$_2$. The combined CH$_2$Cl$_2$ extracts were dried and concentrated to give a colorless oil. The crude product was purified by column chromatography (silica gel, 15-35% EtOAc in hexanes).

The Z-isomer compound 12a (15 mg, 5.3%) eluted second from the column: mp 228-230° C.; IR ν$_{max}$ 2922, 2209, 1731, 1702, 1595 cm$^{-1}$; $^1$H NMR δ 5.01 (b s, 1H), 3.27 (d, 1H, J=12.6 Hz), 2.60-2.25 (m, 4H), 2.05 (s, 3H), 1.84 (b s, 3H), 1.03 (s, 3H), 0.89 (s, 3H); $^{13}$C NMR δ 208.7, 170.6, 167.1, 118.5, 98.2, 69.8, 64.4, 54.8, 53.5, 49.0, 39.9, 35.5 (2×C), 32.3 (2×C), 31.5, 31.1, 27.6, 25.8, 23.2, 21.5, 18.2, 18.0, 11.1. Anal. Calcd for $C_{24}H_{33}NO_3$: C, 75.16%; H, 8.67%; N, 3.65%. Found: C, 75.33%; H, 8.79%, N, 3.47%.

The E-isomer compound 12b (60 mg, 21%) eluted first from the column: mp 166-168° C.; IR ν$_{max}$ 2929, 2209, 1732, 1705 cm$^{-1}$; $^1$H NMR δ 4.99 (b s, 1H), 2.78 (d, 1H, J=12.4 Hz), 2.71 (m, 1H), 2.55 (d, 1H, J=12.4 Hz), 2.25 (m, 1H), 2.03 (s, 3H), 1.87 (b s, 3H), 1.00 (s, 3H), 0.86 (s, 3H); $^{13}$C NMR δ 208.9, 170.5, 166.7, 119.7, 100.7, 69.7, 64.4, 55.2, 54.7. 49.2, 39.8, 35.4, 35.2, 33.2, 32.3, 32.2, 31.5, 27.5, 25.7, 23.6, 21.5, 17.0, 15.1, 11.0. Anal. Calcd for $C_{24}H_{33}NO_3$: C, 75.16%; H, 8.67%; N, 3.65%. Found: C, 75.33%; H, 8.66%, N, 3.60%.

[3α,5β,17(20)Z]-3-Hydroxy-11-oxo-pregn-17(20)-ene-21-nitrile (Compound 13a) and [3α,5β,17(20)E]-3-Hydroxy-11-oxo-pregn-17(20)-ene-21-nitrile (Compound 13b). Diethyl(cyanomethyl)phosphonate (1.6 mmol, 0.26 mL) was added dropwise to a suspension of NaH (60% in dispersion oil, 1.5 mmol, 62 mg) in dry THF (10 mL) at 0° C. under a N$_2$ atmosphere. After disappearance of the NaH, the known (3α, 5β)-3-hydroxyandrostan-11,17-dione (157 mg, 0.52 mmol) in dry THF (25 mL) was added dropwise. This mixture was allowed to attain room temperature and stirred overnight. Then, the reaction mixture was poured into a solution of ammonium chloride and the product was extracted into EtOAc (2×100 mL). The combined organic layers were washed with brine and dried over anhydrous Na$_2$SO$_4$. After solvent removal, the residue was purified by flash column chromatography (silica gel eluted with 10-25% EtOAc/hexanes) to afford slightly impure Compound 13b (57 mg), a mixture of Compound 13a and Compound 13b (22 mg), and pure Compound 13a (55 mg, 32%). The slightly impure Compound 13b (57 mg) and the mixture of Compound 13a and Compound 13b (22 mg) were subsequently repurified on three prep-TLC plates run in EtOAc/toluene (1:2) to afforded pure Compound 13b (46 mg, 27%).

[3α,5β,17(20)Z]-3-Hydroxy-11-oxo-pregn-17(20)-ene-21-nitrile (Compound 13a): mp 219-221° C. (EtOAc/hexanes); $[\alpha]^{20}_D$ +28.0 (c 0.11, CHCl$_3$); IR $v_{max}$ 3272, 2975, 2926, 2866, 2847, 2216, 1699, 1636 cm$^{-1}$; $^1$H NMR δ 5.17 (1H, t, J=2.4 Hz), 3.65 (1H, m), 3.21 (1H, d, J=12.6 Hz), 2.44-2.76 (5H, m), 1.17 (3H, s), 0.91 (3H, s); $^{13}$C NMR δ 208.8, 175.6, 115.9, 89.5, 71.5, 54.6, 53.5, 52.1, 49.7, 42.9, 36.5, 36.1, 34.6, 34.3, 32.7, 31.4, 27.0, 26.6, 23.7, 23.3, 18.3. Anal. Calcd for C$_{21}$H$_{29}$NO$_2$: C, 77.02%; H, 8.93%; N, 4.28%. Found. C, 76.90%; H, 8.94%; N, 4.12%.

[3α,5β,17(20)E]-3-Hydroxy-11-oxo-pregn-17(20)-ene-21-nitrile (Compound 13b): mp 161-163° C. (Et$_2$O/hexanes); $[\alpha]^{20}_D$ −1.51 (c 0.23, CHCl$_3$); IR $v_{max}$ 3393, 2925, 2862, 2216, 1704, 1638 cm$^{-1}$; $^1$H NMR δ 4.98 (1H, t, J=2.4 Hz), 3.65 (1H, m), 3.65 (1H, m), 2.73-2.81 (2H, m), 1.16 (3H, s), 0.81 (3H, s); $^{13}$C NMR δ 208.7, 177.6, 116.9, 89.3, 71.5, 53.5, 53.4, 52.3, 49.5, 42.9, 36.6 (2×C), 34.6, 34.4, 31.4, 30.8, 26.9, 26.6, 23.8, 23.3, 19.2. Anal. Calcd for C$_{21}$H$_{29}$NO$_2$: C, 77.02%; H, 8.93%; N, 4.28%. Found. C, 77.37%; H, 8.80%; N, 4.19%.

[3α,5α,17(20)Z]-3-Hydroxypregn-17(20)-ene-21-nitrile (Compound 14a) and [3α,5α,17(20)E]-3-Hydroxypregn-17(20)-ene-21-nitrile (Compound 14b). Diethyl(cyanomethyl) phosphonate (0.97 mL, 6 mmol) was added dropwise to a suspension of NaH (60% dispersion in oil, 5.5 mmol, 220 mg) in dry THF (25 mL) at 0° C. under a N$_2$ atmosphere and the resulting mixture was allowed to stir until it became homogenous (ca. 0.5 h). Then, (3α,5α)-3-hydroxyandrostan-17-one (androsterone, 400 mg, 1.38 mmol) in THF (15 mL) was added and the mixture was stirred for 18 h at room temperature. Saturated ammonium chloride solution (50 mL) was added to the reaction mixture and the product was extracted with EtOAc. The combined extracts were dried over anhydrous Na$_2$SO$_4$ and the solvents removed to give a colorless liquid. Purification by flash column chromatography (silica gel eluted with 35% EtOAc in hexanes) gave the white solid product (389 mg, 90%) as a mixture of Compound 14a and Compound 14b.

When the unseparated product stereoisomers were crystallized from 50% EtOAc in hexanes, a crystalline white solid (140 mg) which is enriched with 90% of Compound 14a was obtained. Further sequential recrystallizations of the Compound 14a enriched crystals from Et$_2$O in hexanes yielded pure Compound 14a (50 mg).

The mother liquors from the initial 50% EtOAc in hexanes recrystallization was evaporated to give a solid (250 mg) enriched in Compound 14b. Washing this solid with warmed Et$_2$O (10 mL) dissolved mostly the Compound 14b leaving behind a solid further enriched in Compound 14a. Addition of hexanes to the separated Et$_2$O solution supernatant produced, on standing, crystals (80 mg) that were analyzed by $^1$H NMR and found to contain the Compound 14b and Compound 14a in about a 9:1 ratio. Flash column chromatography (silica gel eluted with 20-30% EtOAc in hexanes) of this material yielded, in the early eluting fractions, pure Compound 14b (22 mg).

[(3α,5α,17(20)Z]-3-Hydroxypregn-17(20)-ene-21-nitrile (Compound 14a): mp 261-262° C.; $[\alpha]^{20}_D$ +53.5 (c 0.01, CHCl$_3$); IR $v_{max}$ 3509, 2966, 2915, 2835, 2219, 1630, 1448, 1415, 1378, 1261 cm$^{-1}$; $^1$H NMR δ 5.09 (t, 1H, J=2.2 Hz), 4.05 (bs, 1H), 2.66-2.34 (m, 3H), 0.95 (s, 3H), 0.80 (s, 3H); $^{13}$C NMR δ 179.5, 116.7, 87.7, 66.4, 55.1, 54.0, 46.7, 39.0, 36.1, 35.7, 35.0, 34.7, 32.4, 32.0, 31.7, 29.0, 28.3, 23.7, 20.6, 16.89, 11.1; Anal. Calcd for C$_{21}$H$_{31}$NO: C, 80.46%; H, 9.97%; N, 4.47%. Found: C, 80.57%; H, 10.16%; N, 4.40%.

[(3α,5α,17(20)E]-3-Hydroxypregn-17(20)-ene-21-nitrile (Compound 14b): mp 187-189° C.; $[\alpha]^{20}_D$ −8.24 (c 0.0.09, CHCl$_3$); IR $v_{max}$ 3436, 2921, 2853, 2216, 1637, 1450, 1371, 1268 cm$^{-1}$; $^1$H NMR δ 4.98 (t, 1H, J=2.5 Hz), 4.05 (bs, 1H), 2.80-2.50 (m, 2H), 0.83 (s, 3H), 0.80 (s, 3H); $^{13}$C NMR δ 181.2, 117.5, 87.6, 66.4, 54.1, 53.9, 46.2, 39.0, 36.2, 35.8, 35.2, 34.7, 32.1, 31.6, 30.2, 28.9, 28.3, 23.7, 20.4, 18.0, 11.2. Anal. Calcd for C$_{21}$H$_{31}$NO: C, 80.46%; H, 9.97%; N, 4.47%. Found: C, 80.41%; H, 9.91%; N, 4.31%.

[3α,5β,17(20)Z]-3-Hydroxypregn-17(20)-ene-21-nitrile (Compound 15a) and [(3α,5β,17(20)E]-3-Hydroxypregn-17(20)-ene-21-nitrile (Compound 15b) Diethyl(cyanomethyl) phosphonate (16.6 mmol, 2.7 mL) was added dropwise to a suspension of NaH (60% dispersion in oil, 1.57 mmol, 628 mg) in dry THF (120 mL) at 0° C. under a N$_2$ atmosphere. After disappearance of the NaH, (3α,5β)-3-hydroxyandrostan-17-one (etiocholanolone, 2.69 g, 9.26 mmol) in dry THF (60 mL) was added dropwise. This mixture was allowed to attain room temperature and stirred overnight. The reaction mixture was then poured into a solution of ammonium chloride and the product was extracted twice with EtOAc. The combined extracts were washed with brine and dried over anhydrous Na$_2$SO$_4$. After evaporation of the solvents, the residue (4.7 g) was purified by flash column chromatography (silica gel eluted with 10% EtOAc in hexanes) to give the product as a mixture of Compound 15a and Compound 15b (2.03 g, 70%). Further chromatography and recrystallization from EtOAc gave each of the separated Compound 15a and Compound 15b stereoisomers.

[(3α,5β,17(20Z)]-3-Hydroxypregn-17(20)-ene-21-nitrile (Compound 15a): mp 189-191° C. (EtOAc), $[\alpha]^{20}_D$ +68.4 (c 0.26, CHCl$_3$). IR $v_{max}$ 3306, 2929, 2860, 2215, 1634 cm$^{-1}$; $^1$H NMR δ 4.99 (1H, t, J=2.1 Hz), 3.64 (1H, m), 2.33-2.7 (2H, m), 0.95 (3H, s), 0.94 (3H, s); $^{13}$C NMR δ 179.6, 116.9, 87.9, 71.8, 55.3, 47.0, 42.2, 40.5, 36.5, 35.6, 35.5, 35.1, 34.8, 32.7, 30.7, 27.2, 26.4, 23.9, 23.4, 20.8, 17.1. Anal. Calc for C$_{21}$H$_{31}$NO: C, 80.46%; H, 9.97%; N, 4.47%. Found. C, 80.31%; H, 10.00%; N, 4.21%.

[(3α,5β,17(20)E]-3-Hydroxypregn-17(20)-ene-21-nitrile (Compound 15b): mp 88-90° C. (from EtOAc); $[\alpha]^{20}_D$ +12.6 (c 0.65, CHCl$_3$); IR $v_{max}$ 3368, 2930, 2861, 2216, 1635 cm$^{-1}$; $^1$H NMR δ 4.99 (1H, t, J=2.7 Hz), 3.64 (1H, m), 2.52-2.78 (2H, m), 0.95 (3H, s), 0.83 (3H, s); $^{13}$C NMR δ 181.3, 117.7, 87.85, 71.8, 54.1, 46.5, 42.2, 40.7, 36.5, 35.8, 35.5, 35.1, 34.9, 30.7, 30.5, 27.1, 26.4, 23.9, 23.5, 20.7, 18.2. Anal. Calc for C$_{21}$H$_{31}$NO: C, 80.46%; H, 9.97%; N, 4.47%. Found. C, 80.34%; H, 10.09%; N, 4.36%.

(2β,3α,5α)-3-Hydroxy-2-methoxyandrostan-17-one. Concentrated H$_2$SO$_4$ (0.5 ml) in CH$_3$OH (2 mL) was added to a solution of the known (2α,3α,5α)-2,3-epoxyandrostan-17-one epoxide (292 mg, 1.0 mmol) in CH$_3$OH (10 mL) at 0° C. After 30 min, the mixture was warmed to room temperature for an additional 30 min. The reaction was terminated by addition of aqueous NaHCO$_3$ and the steroids extracted into EtOAc (50 ml×3). The combined organic layers were dried, filtered, and concentrated. The residue was purified by flash column chromatography (silica gel eluted with 25% EtOAc in hexanes) to afford the product (206 mg, 73%): mp 151-153° C.; $[\alpha]_D^{20}$+92.4 (c 0.37, CHCl$_3$); IR $v_{max}$ 3439, 1738, 1453, 1092 cm$^{-1}$; $^1$H NMR (CDCl$_3$) δ 3.84-3.83 (m, 1H), 3.22 (s, 4H), 2.53 (br s, 1H), 0.86 (s, 3H), 0.76 (s, 3H), 0.71-0.64 (m, 1H); $^{13}$C NMR (CDCl$_3$) δ 221.4, 80.5, 67.7, 56.4, 54.9, 51.3, 47.6, 38.7, 35.9, 35.6, 35.2, 34.3, 31.8, 31.4, 30.6, 27.6, 21.5, 19.9, 13.6, 12.9. Anal. Calcd for C$_{20}$H$_{32}$O$_3$: C, 74.76%; H, 10.06%. Found: C, 75.04%; H, 9.93%.

[2β,3α,5α,17(20)Z]-3-Hydroxy-2-methoxyandrost-17 (20)-ene-21-nitrile (Compound 16a) and [2β,3α,5α,17(20) E]-3-Hydroxy-2-methoxyandrost-17(20)-ene-21-nitrile (Compound 16b). Diethyl(cyanomethyl)phosphonate (974 mg, 5.5 mmol) was added to a suspension of NaH (200 mg, 60% in mineral oil, 5 mmol) in THF (10 mL) at room temperature. After 10 min, (2β,3α,5α)-3-Hydroxy-2-methoxyandrostan-17-one (100 mg, 0.31 mmol) in THF (5 mL) was added. The mixture was stirred at room temperature for 16 h. The mixture was terminated by addition of aqueous $NH_4Cl$ and the products extracted into EtOAc (50 mL×3). The combined organic layers were dried, filtered, and concentrated. The residue was purified by column flash chromatography (silica gel eluted with 25% EtOAc in hexanes) to afford products Compound 16a and Compound 16b (105 mg, ratio ~1/1, 98%). Three recrystallizations (ether and hexanes) afforded pure Compound 16a (26 mg).

[2β,3α,5α,17(20)Z]-3-Hydroxy-2-methoxyandrost-17 (20)-ene-21-nitrile (Compound 16a): mp 170-172° C.; $[\alpha]_D^{20}$+39.0 (c 0.10, $CHCl_3$); IR $v_{max}$ 3429, 2214, 1635, 1454, 1092 $cm^{-1}$; $^1H$ NMR ($CDCl_3$) δ 5.08 (s, 1H), 3.95-3.90 (m, 1H), 3.30-3.34 (m, 1H), 3.32 (s, 3H), 0.94 (s, 6H), 1.02-0.87 (m, 2H), 0.79-0.74 (m, 1H); $^{13}C$ NMR ($CDCl_3$) δ 179.5, 116.8, 87.7, 80.6, 68.2, 56.7, 55.0, 54.7, 46.8, 38.9, 36.0, 35.4, 34.6, 34.4, 32.4, 32.0, 31.7, 27.8, 23.6, 20.7, 16.9, 13.0. HRMS m/z Calcd for $C_{22}H_{33}O_2$: 343.2511. Found: 343.2519.

The mother liquors from the three recrystallizations that gave pure Compound 16a were combined and the solvents removed to give a mixture of Compound 16b and Compound 16a (80 mg, E/Z ratio ~1.6). This product mixture was dissolved in $CH_3OH$, $K_2CO_3$ (1.38 g, 10 mmol) was added and the reaction was refluxed for 2 h. After cooling to room temperature, water was added and the products extracted into EtOAc (50 mL×3). The combined organic layers were dried, filtered, and concentrated. The residue was purified by flash column chromatography (silica gel eluted with 25% EtOAc in hexanes) to afford Compound 16b containing ~10% Compound 16a as determined by $^1H$ NMR (80 mg, 100%). Three recrystallizations (ether and hexanes) afforded pure Compound 16b (28 mg).

[2β,3α,5α,17(20)E]-3-Hydroxy-2-methoxyandrost-17 (20)-ene-21-nitrile (Compound 16b): mp 135-137° C.; $[\alpha]_D^{20}$-4.3 (c 0.10, $CHCl_3$); IR $v_{max}$ 3450, 2216, 1635, 1449, 1092 $cm^{-1}$; $^1H$ NMR ($CDCl_3$) δ 4.97 (t, J=2.3 Hz, 1H), 3.94 (d, J=2.3 Hz, 1H), 3.30-3.34, (m, 1H), 3.32 (s, 3H), 2.71-2.52 (m, 2H), 0.93 (s, 3H), 0.81 (s, 3H), 0.76-0.69 (m, 1H); $^{13}C$ NMR ($CDCl_3$) δ 181.2, 117.5, 87.5, 80.6, 68.0, 56.7, 54.8, 53.8, 46.2, 38.9, 36.0, 35.5, 34.7, 34.6, 32.0, 31.6, 30.2, 27.8, 23.7, 20.5, 18.0, 13.1. HRMS m/z Calcd for $C_{22}H_{33}O_2$: 343.2511. Found: 343.2500.

(3α,5α,11β)-(3-Methoxymethoxy)-11-methoxy-androstan-17-one, cyclic 17-(1,2-ethanediyl acetal). A mixture of the known (3α,5α,11β)-(3-methoxymethoxy)-11-hydroxyandrostan-17-one, cyclic 17-(1,2-ethanediylacetal) (400 mg, 1.01 mmol), sodium hydride (200 mg, 5 mmol) and THF (10 mL) was heated at reflux for 2 h under a $N_2$ atmosphere. The reaction was cooled to room temperature, and methyl iodide (2 mL, 32 mmol) was added and the reaction was then stirred at 40° C. for 2 h, cooled to room temperature and stirred for another 13 h. The reaction was then cooled to 0° C. and excess sodium hydride carefully eliminated by adding methanol (2 mL). Water (80 mL) was added to the mixture and the product extracted into EtOAc (70 mL×3). The combined organic extracts were washed with brine, dried and concentrated to give a colorless liquid. The crude product was purified by flash column chromatography (silica gel eluted with 15-20% EtOAc in hexanes) to give the methyl ether product as a colorless liquid (405 mg, 99%): IR $v_{max}$ 2926, 1458, 1369, 1304, 1229, 1212 $cm^{-1}$; $^1H$ NMR δ 4.58 (s, 2H), 3.86-3.64 (m, 5H), 3.62 (s, 1H), 3.29 (s, 3H), 3.13 (s, 3H), 0.93 (s, 3H), 0.90 (s, 3H); $^{13}C$ NMR δ 119.3, 94.4, 77.0, 71.5, 64.9, 64.2, 58.0, 55.1, 54.9, 51.9, 45.2, 40.3, 35.9, 33.8, 33.0, 32.5, 31.8 (2×C), 31.0, 27.8, 26.0, 22.4, 15.2, 13.9. Anal. Calcd for $C_{24}H_{40}O_5$: C, 70.55%; H, 9.87%. Found: C, 70.80%; H, 9.60%.

(3α,5α,11β)-3-Hydroxy-11-methoxyandrostan-17-one. (3α,5α,11β)-(3-Methoxymethoxy)-11-methoxy-androstan-17-one, cyclic 17-(1,2-ethanediylacetal) (340 mg, 0.83 mmol), methanol (12 mL) and 6 N HCl (2 mL) was stirred at room temperature for 18 h. The methanol was removed under reduced pressure and the residual solution was diluted with water (50 mL) and extracted with EtOAc (3×50 mL), dried and concentrated to give a viscous liquid, which was purified by flash column chromatography (silica gel eluted with 35-45% EtOAc in hexanes) to give the 17-ketone product as a foam (260 mg, 97%): IR $v_{max}$ 3441, 2923, 1739, 1457, 1370, 1240 $cm^{-1}$; $^1H$ NMR δ 3.97 (br s, 1H), 3.67 (br s, 1H), 3.16 (s, 3H), 0.96 (s, 3H), 0.91 (s, 3H); $^{13}C$ NMR δ 220.3, 76.6, 66.0, 58.5, 55.3, 53.0, 47.1, 39.7, 36.2, 35.2, 35.2, 32.2, 31.8, 31.3, 31.2, 28.5, 27.6, 21.4, 14.5, 13.7. Anal. Calcd for $C_{20}H_{32}O_3$: C, 74.96%; H, 10.06%. Found: C, 74.72%; H, 9.99%.

[3α,5α,11β,17(20)Z]-3-Hydroxy-11-methoxypregn-17 (20)-ene-21-nitrile (Compound 17a) and [3α,5α,11β,17(20) E]-3-Hydroxy-11-methoxypregn-17(20)-en-21-nitrile (Compound 17b). Diethyl(cyanomethyl)phosphonate (1.7 mL, 10.3 mmol) was added dropwise to a suspension of NaH (60% dispersion in oil, 400 mg, 10 mmol) in dry THF (12 mL) at 0° C. under $N_2$. After disappearance of the NaH, (3α,5α, 11β)-3-Hydroxy-11-methoxyandrostan-17-one (200 mg, 0.62 mmol) in dry THF (10 mL) was added. This mixture was allowed to warm to room temperature and stirred for another 15 h at room temperature. The reaction was quenched with aqueous $NaHCO_3$ and the product extracted into EtOAc. The combined EtOAc extracts were washed with brine and dried. After solvent evaporation, the residue was purified by flash column chromatography to give an inseparable mixture of Compound 17a and Compound 17b (180 mg 85%).

In order to separate Compound 17a and Compound 17b (120 mg, 0.34 mmol) the compounds were converted into their corresponding 3-acetates (120 mg, 91%) using typical acetylation reagents (AcOAc, $(Et)_3N$, 4-DMAP in $CH_2Cl_2$). These 3-acetate derivatives were separated by preparative TLC (6 plates, run in $CH_2Cl_2$). Iodine vapors from iodine crystals were used to visualize the separated compounds on the TLC plates. By this purification method ~70% pure 3-acetate of Compound 17a (35 mg, the more polar band) containing ~30% of the less polar Compound 17b and ~65% pure Compound 17b (40 mg, the less polar band) containing ~35% of the more polar Compound 17a and some additional mixture of the 3-acetates (30 mg) were obtained.

The 70% pure 3-acetate derivative of Compound 17a (35 mg) was subjected to transesterification (using dry HCl/MeOH) to give 70% pure Compound 17a (28 mg, 90%). This product was crystallized twice from $Et_2O$-hexanes to give pure Compound 17a (18 mg, 58%): mp 200-202° C.; $[\alpha]^{20}_D$=+25.0 (c 0.09, $CHCl_3$); IR $v_{max}$ 3307, 2962, 2925, 2212, 1632, 1461, 1381 $cm^{-1}$; $^1H$ NMR δ 4.98 (t, 1H, J=2.0 Hz), 3.98 (t, 1H, J=2.4 Hz), 3.68 (q, 1H, J=3.0 Hz), 3.21 (s, 3H), 2.94 (dd, 1H, J=14.5, 2.3 Hz), 2.73-2.65 (m, 1H), 2.58-2.51 (m, 1H), 2.33-2.50 (m, 1H), 1.04 (s, 3H), 0.91 (s, 3H); $^{13}C$ NMR δ 179.5, 116.9, 87.2, 76.8, 66.4, 58.2, 56.7, 55.6, 55.6, 46.3, 39.8, 36.3, 35.4, 35.2, 32.3, 32.1, 31.9, 31.3, 28.7, 27.8, 23.5, 17.9, 13.9. Anal. Calcd for: $C_{22}H_{33}NO_2$, C, 76.92%; H, 9.68%; N, 4.08. Found: C, 77.12%; H, 9.50%; N, 4.03.

A mixture of the unseparated 3-acetate derivatives of Compound 17a and Compound 17b (65 mg) was subjected to deacetylation and isomerization to increase the amount of the thermodynamically more stable Compound 17b by refluxing in MeOH (5 mL) in presence of $K_2CO_3$ (100 mg) for 15 h. Removal of MeOH gave a residue to which water (50 mL) was added and the products extracted into $CH_2Cl_2$ (3×60 mL). The combined $CH_2Cl_2$ extracts were washed with brine dried and concentrated to give a white solid. This solid was purified by passing through a short column of silica gel to give 90% enriched Compound 17b (50 mg). This 90% pure Compound 17b was crystallized from $EtO_2$-hexanes (twice) to give pure Compound 17b (25 mg, 43%): mp 194-196° C.; $[\alpha]^{20}_D$ −12.8 (c 0.09, $CHCl_3$); IR $v_{max}$ 3519, 2921, 2851, 2220, 1633, 1459, 1369, 1263 $cm^{-1}$; $^1H$ NMR δ 4.94 (t, 1H, J=2.8 Hz), 4.03 (t, 1H, J=2.3 Hz), 3.71 (q, 1H, J=3.0 Hz), 3.22 (s, 3H), 2.73-2.65 (m, 1H), 2.58-2.50 (m, 1H), 2.22 (dd, 1H, J=13.7, 2.3 Hz), 0.97 (s, 3H), 0.95 (s, 3H); $^{13}C$ NMR δ 181.1, 117.6, 87.1, 76.7, 66.4, 58.3, 55.6, 55.5, 45.7, 39.8, 36.4, 35.3, 35.3, 32.2, 32.0, 28.7, 27.7, 23.6, 19.0, 13.8. Anal. Calcd for: $C_{22}H_{33}NO_2$: C, 76.92%; H 9.68%; N, 4.08. Found: C, 76.84%; H, 9.50%; N, 4.13%.

[$^{35}S$]-TBPS Displacement

The $IC_{50}$ values for the compounds of charts 1 and 2 (i.e., Compounds 1-6d and 13a-17b) as non-competitive displacers of [$^{35}S$]-TBPS from the picrotoxin binding site on $GABA_A$ receptors are reported in Table 1.

TABLE 1

Inhibition of [$^{35}S$]-TBPS Binding by Alphaxalone, $\Delta^{16}$-Alphaxalone and Structural Analogues[a]

| Compound | $IC_{50}$ (nM) | $n_{Hill}$ |
| --- | --- | --- |
| 1[b] | 226 ± 24 | 1.10 ± 0.11 |
| 2[b] | 2,220 ± 260 | 1.24 ± 0.14 |
| 3[b] | 190 ± 18 | 1.14 ± 0.11 |
| 4[b] | 361 ± 58 | 1.00 ± 0.14 |
| 5a | 997 ± 187 | 1.50 ± 0.36 |
| 5b | 770 ± 98 | 0.97 ± 0.10 |
| 5c | 1,020 ± 204 | 0.94 ± 0.14 |
| 6a | 128 ± 11 | 1.44 ± 0.15 |
| 6b | 2,030 ± 810 | 0.90 ± 0.23 |
| 6c | 629 ± 89 | 1.48 ± 0.25 |
| 6d | 1,840 ± 480 | 1.46 ± 0.42 |
| 13a | 474 ± 35 | 0.94 ± 0.06 |
| 13b | 9,600 ± 2,500 | 1.20 ± 0.19 |
| 14a | 25 ± 3 | 1.09 ± 0.14 |
| 14b | 501 ± 39 | 0.97 ± 0.06 |
| 15a | 56 ± 10 | 0.94 ± 0.14 |
| 15b | 1,200 ± 400 | 1.10 ± 0.34 |
| 16a | 28 ± 2 | 1.09 ± 0.05 |
| 16b | 544 ± 87 | 0.86 ± 0.10 |
| 17a | 53 ± 7 | 1.51 ± 0.21 |
| 17b | 605 ± 139 | 1.27 ± 0.30 |

[a]Results presented are from duplicate experiments performed in triplicate. Error limits are calculated as standard error of the mean. Methods used are known in the art (see Jiang, X., et al., *Neurosteroid analogues*. 9. Conformationally constrained pregnates: structure-activity studies of 13,24-cyclo-18,21-dinorcholane analogues of the GABA modulatory and anesthetic steroids (3α, 5α)- and (3α, 5α)-hydroxypregnan-20-one. J. Med. Chem., 46: 5334-48 (2003)).
[b]These values were obtained from Bandyopadhyaya, et al.

Compounds 1-4 were the reference compounds for this study and the binding results reported are those discussed in Bandyopadhyaya, et al. Compound 5a is the C-17 aldehyde analogue of Compounds 2 and 4. Comparison of the $IC_{50}$ values for [$^{35}S$]-TBPS displacement potency for Compounds 2 and 5a shows that changing the C-17 acetyl group to an aldehyde group improves displacement potency by about twofold. Compound 5b, which lacks the $\Delta^{16}$ double bond, is about equal to Compound 5a as a displacer of [$^{35}S$]-TBPS. Thus, it appears that the $\Delta^{16}$ double bond has no adverse effect on displacement potency when the compound does not contain a C-21 methyl group. A comparison of the $IC_{50}$ values for Compounds 3 and 4 leads to a similar conclusion when the C-17 substituent is a nitrile group. Comparison of the $IC_{50}$ values for Compounds 4 and 5a shows about a threefold difference in potency in favor of Compound 4. A comparison of the $IC_{50}$ values of Compounds 3 and 5c indicates that moving the nitrile group off of the steroid D-ring into a side chain that can undergo free rotation lowers potency for [$^{35}S$]-TBPS displacement about fivefold.

Figure 2:
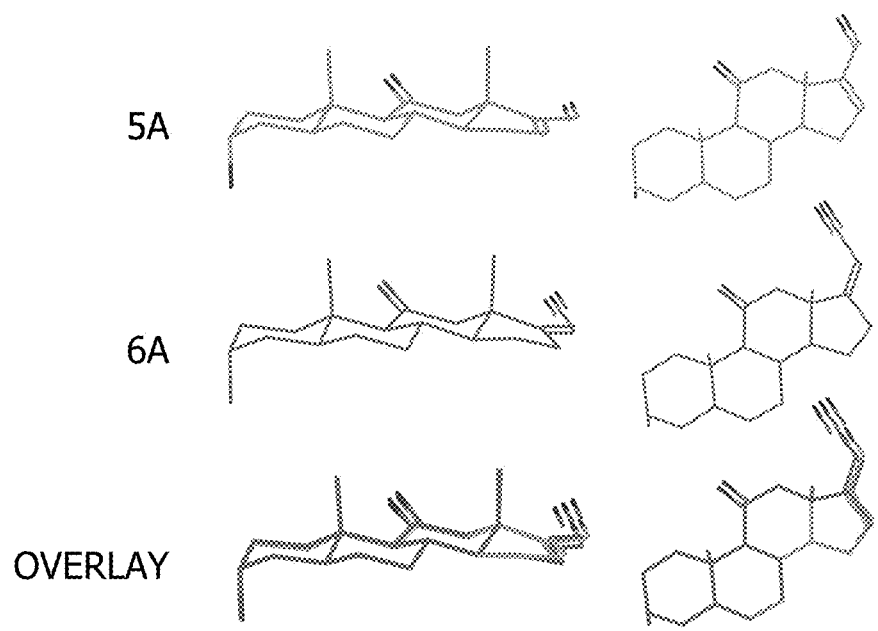
FIG. 2 contains molecular models showing that Compounds 5a (top) and 6a (middle) are isosteric (bottom). (Left column=edge view. Right column=top view.)

Compound 6a is an isosteric analogue of Compound 5a. The 6a nitrile group lies along the axis of the atoms in the carbonyl group of Compound 5a (see FIG. 2). Additionally, the nitrile and carbonyl groups are both hydrogen bond acceptors. The [$^{35}S$]-TBPS displacement results obtained with Compounds 2 and 5a suggest that compound 6a should have an $IC_{50}$ value more similar to that of Compound 5a than to that of Compound 2 since Compound 6a does not have a C-21 methyl group. Indeed, this was found to be the case with Compound 6a being about eightfold more potent than Compound 5a, but about 17-fold more potent than Compound 2. Surprisingly, Compound 6a was about twofold more potent than the clinically used steroid anesthetic alphaxalone (Compound 1). Additionally, Compound 6a has an $IC_{50}$ value very similar to that of Compound 4 in spite of the fact that the nitrile group in each steroid is oriented differently with respect to the axis of a vector passing through the mid-point of the C-14, C-15 and C-17 bond.

Comparison of the $IC_{50}$ values of Compounds 6a (Z isomer) and 6b (E isomer) indicates that interchanging the relative positions of the C-20 substituents (H, CN) has a large effect on [$^{35}S$]-TBPS displacement potency. Compound 6a was about 17-fold more potent at displacing [$^{35}S$]-TBPS than Compound 6b. A comparison of the $IC_{50}$ values for Compounds 6a, 6b and 5c shows the effect that hydrogenation of the $\Delta^{17(20)}$ double bond present in Compound 6a and 6b has on binding potency. The change in conformation of the D-ring and the loss of the steric restraint imposed by the $\Delta^{17(20)}$ double bond increased the $IC_{50}$ value of Compound 5c about eightfold relative to Compound 6a, and decreased the $IC_{50}$ value about twofold relative to Compound 6b.

The disparity in displacement potency between Z and E isomers noted above was also observed in compounds 13-17, the Z isomer being about 10- to 20-fold more potent than the E isomer. Comparison between 6a and 13a, and between 14a and 15a seemed to suggest that isomers with C-5 α-configuration (6a and 14a) may be more potent than those with C-5 β-configuration (13a and 15a). Moreover, comparison between 6a, 14a, and 17a seemed to suggest that C-11 substitution may also affect the potency, with C-11H (14a) being about 2-fold stronger than C-11 MeO (17a) and about 5-fold stronger than C-11 carbonyl (6a).

Compound 6c (Z isomer) is an analogue of Compound 2 (the nitrile group replaces the carbonyl group) in its minimum energy conformation and compound 6d (E isomer) is an analogue of Compound 2 in its high energy U-conformation (i.e., the conformation in which the relative positions of the carbonyl and C-21 methyl groups are interchanged). The compounds differ from the 6a and 6b analogues only by the presence of the C-21 methyl group in their structures. A comparison of Compound 6a and 6c shows displacement potency is decreased about fivefold by the C-21 methyl group. By contrast, a comparison of Compound 6b and 6d shows no significant effect on displacement potency. Thus, the C-21 methyl group has a negative effect on the [$^{35}$S]-TBPS displacement potency of the Z isomer (6c), but little effect on the [$^{35}$S]-TBPS displacement potency of the E isomer (Compound 6d).

Electrophysiology Results

The compounds of the present disclosure were evaluated for the ability to potentiate chloride currents mediated by 2 μM GABA at rat $\alpha_1\beta_2\gamma_{2L}$ type GABA$_A$ receptors expressed in *Xenopus laevis* oocytes and the results are shown in Table 2.

TABLE 2

Modulation of Rat $\alpha_1\beta_2\gamma_{2L}$ GABA$_A$ Receptor Function by Alphaxalone, $\Delta^{16}$-Alphaxalone and Structural Analogues.

| Compound | oocyte electrophysiology[a] | | | |
|---|---|---|---|---|
| | 0.1 μM | 1 μM | 10 μM | (gating) 10 μM |
| 1[b] | 2.91 ± 0.57 | 4.70 ± 1.11 | 19.64 ± 4.04 | 0.11 ± 0.02 |
| 2[b] | 0.94 ± 0.04 | 0.97 ± 0.05 | 1.87 ± 0.14 | 0.08 ± 0.07 |
| 3[b] | 1.12 ± 0.03 | 4.59 ± 0.42 | 21.14 ± 2.14 | 0.14 ± 0.03 |
| 4[b] | 1.49 ± 0.44 | 4.07 ± 1.09 | 23.75 ± 3.61 | 0.21 ± 0.04 |
| 5a | 0.77 ± 0.06 | 1.57 ± 0.15 | 10.78 ± 0.64 | 0.02 ± 0.01 |
| 5b | 0.87 ± 0.02 | 1.44 ± 0.02 | 8.22 ± 0.14 | 0.04 ± 0.01 |
| 5c | 0.91 ± 0.03 | 1.13 ± 0.08 | 4.67 ± 0.14 | 0.01 ± 0.01 |
| 6a | 1.17 ± 0.04 | 5.06 ± 0.6 | 21.51 ± 7.07 | 0.17 ± 0.00 |
| 6b | 0.79 ± 0.05 | 0.77 ± 0.04 | 1.82 ± 0.21 | 0.02 ± 0.01 |
| 6c | 0.90 ± 0.05 | 1.52 ± 0.24 | 5.02 ± 0.62 | 0.04 ± 0.01 |
| 6d | 0.90 ± 0.01 | 0.86 ± 0.04 | 1.53 ± 0.02 | 0.05 ± 0.02 |
| 13a | 1.00 ± 0.5 | 1.31 ± 0.03 | 8.90 ± 1.32 | 0.01 ± 0.14 |
| 13b | 0.99 ± 0.13 | 0.99 ± 0.09 | 1.06 ± 0.16 | −0.10 ± 0.09 |
| 14a | 2.18 ± 0.19 | 3.28 ± 0.37 | 3.98 ± 0.25 | 0.29 ± 0.32 |
| 14b | 0.76 ± 0.05 | 1.30 ± 0.07 | 3.15 ± 0.38 | −0.14 ± 0.13 |
| 15a | 1.32 ± 0.03 | 5.00 ± 0.30 | 6.82 ± 0.68 | 0.03 ± 0.02 |
| 15b | 0.94 ± 0.02 | 1.24 ± 0.04 | 4.83 ± 0.44 | 0.01 ± 0.01 |
| 16a | 2.14 ± 0.33 | 12.02 ± 2.54 | 18.77 ± 5.16 | 0.40 ± 0.12 |
| 16b | 0.95 ± 0.15 | 1.34 ± 0.07 | 4.81 ± 0.36 | 0.03 ± 0.14 |
| 17a | 2.14 ± 0.28 | 10.28 ± 2.62 | 11.20 ± 3.28 | 0.06 ± 0.07 |
| 17b | 0.99 ± 0.02 | 1.07 ± 0.03 | 3.68 ± 0.17 | 0.01 ± 0 |

[a]The GABA concentration used for the control response was 2 μM. Each compound was evaluated on at least four different oocytes at the concentrations indicated, and the results reported are the ratio of currents measured in the presence/absence of added compound. Gating represents direct current gated by 10 μM compound in the absence of GABA, and this current is reported as the ratio of compound only current/2 μM GABA current. Error limits are calculated as standard error of the mean (N ≥ 4). Methods used are known in the art (see Jiang, X., et al.).
[b]These values were obtained from Bandyopadhyaya, et al.

The measured concentration of GABA, on average, gates about 4% of the maximum response of a cell. However, the sensitivity to GABA of the receptors, which determines the degree of steroid potentiation that can be measured, varied from one batch of oocytes to another. Hence, it is not possible to directly compare the degree of potentiation among analogues shown in Table 2. However, it is useful to compare concentration-response data for individual compounds in the table as an initial way to distinguish highly active from weakly active compounds. Highly active compounds cause increasing potentiation of the 2 μM GABA-mediated response as the concentration of the compound is increased (0.1, 1 and 10 μM). Compounds that are weak potentiators yield flat concentration-response data and frequently only augment GABA-mediated currents at the highest concentration tested (10 μM).

As reported previously, compound 1 is a strong potentiator and its $\Delta^{16}$ analogue Compound 2 is not (see Bandyopadhyaya, et al.). Compound 3 and its $\Delta^{16}$ analogue Compound 4 are both strong potentiators (see Bandyopadhyaya, et al.). Compound 5a, the $\Delta^{16}$ analogue in which the C-17 substituent is an aldehyde, yielded concentration-dependent potentiation, with a strong increment in potentiation at the highest concentration (10 μM). These results differ from those obtained with Compound 2, the $\Delta^{16}$ analogue containing the C-17 acetyl substituent, whose degree of measured potentiation increased minimally when the concentration was increased from 1 μM to 10 μM. As a potentiator, Compound 5a has a profile more similar to that of Compound 4 than to that of Compound 2. These results correlate well with the [$^{35}$S]-TBPS displacement results where Compound 5a was found to be more potent than Compound 2, but less potent than Compound 4 at displacing [$^{35}$S]-TBPS.

Hydrogenation of the $\Delta^{16}$ double bond in Compound 5a had little effect on activity since Compounds 5a and 5b both show a similar potentiation of GABA-mediated currents when their concentrations are increased from 1 μM to 10 μM. The result is in striking contrast to the effect this structural difference has on the GABAergic actions of Compounds 1 and 2, but similar to the effect it has on the GABAergic actions of Compounds 3 and 4. Comparison of the potentiation results for Compounds 3 and 5c shows that having the nitrile group directly attached to C-17 yields the more active compound. All of these results correlate with those found for potency of [$^{35}$S]-TBPS displacement.

Figure 3A:
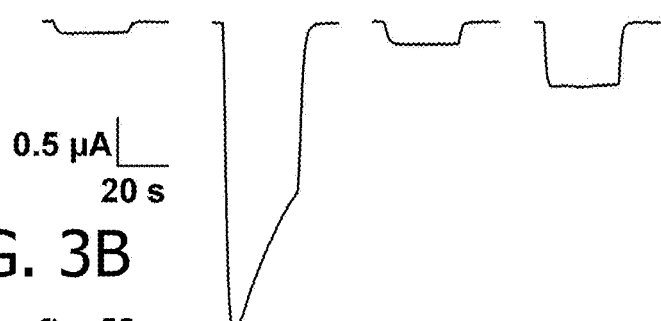
FIGS. 3A and 3B are graphs illustrating a direct quantitative comparison of Compounds 6a, 6b and 5c at 10 μM on responses to GABA in Xenopus oocytes expressing $\alpha_1\beta_2\gamma_{2L}$ $GABA_A$ receptor subunits. (3A: Response to 2 μM GABA alone (left trace) and to GABA co-applied with 10 μM each of 6a (second trace), 6b (third trace), and 5c (right trace). 3B: Summary of responses normalized to the response of GABA alone, indicated with a dotted horizontal line at y=1 (N=4). Error bars are SEM.)
Figure 3B:
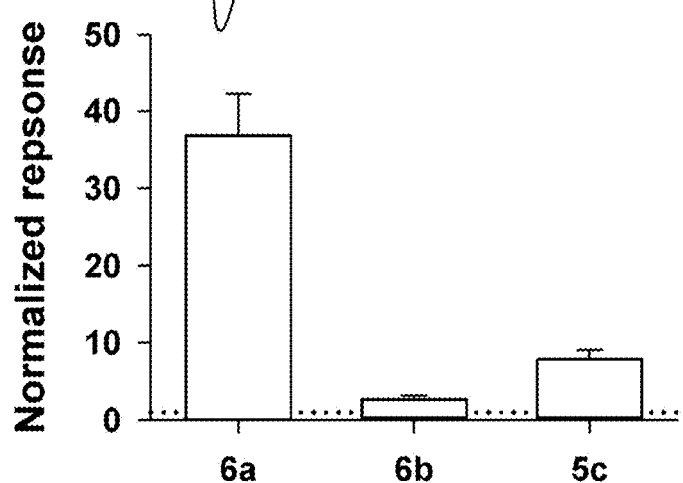
Figure 4:
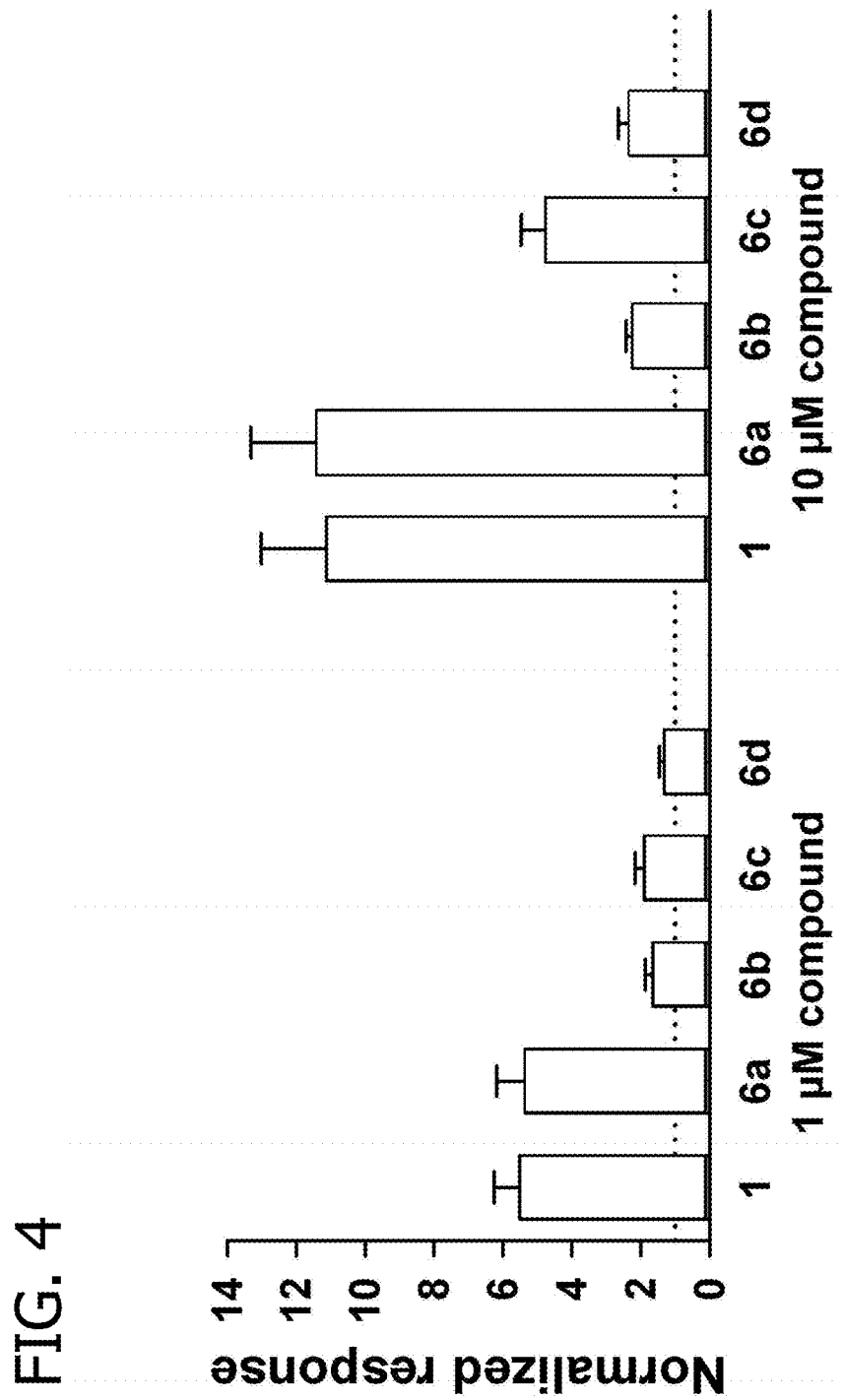
FIG. 4 is a graph illustrating a summary of normalized responses of oocytes to co-applied GABA (2 μM) plus 1 μM (left set of bars) or 10 μM (right set of bars) of the compounds indicated therein. The normalizing response of GABA alone is indicated by the horizontal dotted line at y=1. Bars represent responses of 6 to 7 oocytes for each compound. Error bards are SEM.

Table 2 qualitatively suggests that Compound 6a is a strong potentiator. In order to quantitatively distinguish enhancement differences for Compounds 6a, 6b and 5c, these three compounds were directly compared at a concentration of 10 μM on the same oocytes (FIG. 3). Compound 6a strongly enhanced GABA-mediated currents. These functional results correlate with the order of the IC$_{50}$ values for [$^{35}$S]-TBPS displacement by these compounds. In addition, other Z isomer steroids (e.g., 13a, 15a-17a) showed stronger potency at 10 μM than their E isomer counterparts. Interestingly, 14a (Z isomer) was more potent than 14b (E isomer) at lower concentrations, and was slightly more potent than 14b at 10 μM. Both 14a and 14b were generally less potent than the other Z-isomer steroids tested. The fact that 14a was the most potent Z-isomer in the [35S]-TBPS displacement test, but was the least potent Z-isomer in the electrophysiology test, suggests that compound 14a may potentially be a partial agonist.

Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Effects of Alphaxalone, $\Delta^{16}$-Alphaxalone and Structural Analogues on Tadpole Righting and Swimming Reflexes[a]

| Compound[a] | Tadpole LRR EC$_{50}$ (μM) | Tadpole LRR n$_{Hill}$ | Tadpole LSR EC$_{50}$ (μM) | Tadpole LSR n$_{Hill}$ |
|---|---|---|---|---|
| 1[b] | 1.12 ± 0.14 | −3.38 ± 2.28 | 5.48 ± 0.11 | −33 ± 0[c] |
| 2[b] | >10 | — | None[d] | — |
| 3[b] | 0.72 ± 0.11 | −1.49 ± 0.26 | 5.48 ± 0.12 | −33 ± 0 |
| 4[b] | 1.04 ± 0.14 | −1.77 ± 0.38 | 5.48 ± 0.12 | −33 ± 0 |
| 5a | 3.22 ± 0.03 | −16 ± 1.8 | None | — |
| 5b | 3.98 ± 2.43 | −2.76 ± 3.73 | None | — |
| 5c | 3.58 ± 1.59 | −3.21 ± 5.34 | None | — |
| 6a | 1.44 ± 0.20 | −2.84 ± 0.77 | 5.48 ± 0.20 | −33 ± 0 |
| 6b | 9.15 ± 5.37 | −1.70 ± 1.15 | 17.3 ± 0.17 | −36 ± 0 |
| 6c | 2.71 ± 0.26 | −2.47 ± 0.64 | 5.48 ± 0.20 | −33 ± 0 |
| 6d | 2.09 ± 0.12 | −2.42 ± 0.24 | >10 | — |
| 13a | >10 | — | None | — |
| 13b | >10 | — | None | — |
| 14a | None | — | None | — |
| 14b | 1.21 ± 0.41 | −4.29 ± 6.62 | >10 μM | — |
| 15a | 0.472 ± 0.046 | −2.21 ± 0.34 | 1.0 ± 0 | −18.5 ± 0 |
| 15b | 1.21 ± 0.35 | −4.28 ± 5.67 | 5.48 ± 0.2 | −33.2 ± 0.15 |
| 16a | 0.029 ± 0.006 | −1.57 ± 0.43 | 0.110 ± 0.001 | −18.6 ± 0.4 |
| 16b | 0.29 ± 0.05 | −1.82 ± 0.49 | 2.97 ± 0 | −20.8 ± 0.5 |

TABLE 3-continued

Effects of Alphaxalone, $\Delta^{16}$-Alphaxalone and
Structural Analogues on Tadpole Righting and Swimming Reflexes[a]

| Compound[a] | Tadpole LRR EC$_{50}$ (μM) | Tadpole LRR n$_{Hill}$ | Tadpole LSR EC$_{50}$ (μM) | Tadpole LSR n$_{Hill}$ |
|---|---|---|---|---|
| 17a | 0.067 ± 0.003 | −2.26 ± 0.15 | 0.173 ± 0.003 | −36.3 ± 0.1 |
| 17b | 1.19 ± 0.49 | −6.23 ± 14.2 | 3.17 ± 0.01 | −15.7 ± 0.9 |

[a]Methods used are known in the art (see Jiang, X., et al.). Error limits are calculated as standard error of the mean (N = 10 or more animals at each of five or more different concentrations).
[b]These values were obtained from Bandyopadhyaya, et al.
[c]LSR typically has a very steep dose-response curve and the n$_{Hill}$ values reflect the fact that at 3 μM (10 μM for compound 6b) all or nearly all animals had a swimming response and at 10 μM (30 μM for compound 6b) the animals did not.
[d]"None" indicated that all animals had a swimming response at 10 μM of the test compound.

The results for compounds 1-4 were published previously (see Bandyopadhyaya, et al.). Unlike Compound 2, which did not cause LRR, Compound 5a does cause LRR with an EC$_{50}$ of about 3 μM. The concentration-response curve found for Compound 5a is very steep and unique among the compounds in this study. Compound 5b, the compound produced by hydrogenation of Compound 5a, had LRR and LSR EC$_{50}$ values comparable to those of Compound 5a.

Figure 5:
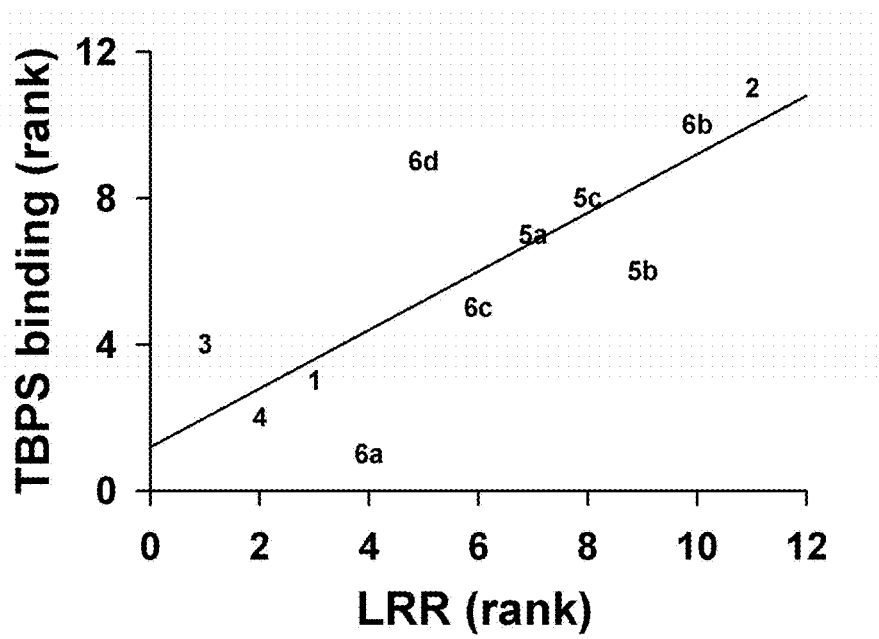
FIG. 5 is a graph illustrating the rank order correlation plot of the analogue [$^{35}$S]-TBPS $IC_{50}$ values with their corresponding tadpole LRR $EC_{50}$ values. Compound numbers are used to represent data points on the plot. The correlation is significant: r =0.8 (p<0.05).

Compound 6a is about eightfold and about threefold more potent than Compound 6b at causing LRR and LSR, respectively. Compounds 6c and 6d have similar tadpole LRR EC$_{50}$ values, but only Compound 6c causes LSR with an EC$_{50}$ below 10 μM. Comparison of tadpole LRR EC$_{50}$ values for the Z isomers 6a and 6c shows that the presence of the C-21 methyl group in the steroid decreases the potency of the Z isomer for tadpole LRR slightly more than twofold. The same comparison for the E isomers 6b and 6d shows that the C-21 methyl group increases the potency of the E isomer slightly more than fourfold. Compound 5c, the hydrogenation product of either Compound 6a or 6b, is less potent than Compound 6a and more potent than steroid 6b at causing tadpole LRR, and it does not cause LSR at concentration 10 μM. FIG. 5 shows a rank order correlation for the [$^{35}$S-TBPS] IC$_{50}$ values and tadpole LRR EC$_{50}$ values for compounds 1 through 6d. The correlation coefficient is 0.8 (p<0.05), which indicates a strong correlation between these parameters. Other Z isomer steroids (e.g., 15a-17a) were also observed to be more potent than their E isomer counterparts (i.e., 15b-17b, respectively), which further supports the difference in potency observed in Z/E isomers 6a and 6b. The lack of anesthetic activity of compound 14a is consistent with the suggestion made from the electrophysiological evaluation that this compound may potentially be a partial agonist. Compound 14a appears to be unique in this regard, among the Z isomers examined here.

Anesthesia in Mice

An assessment of the potency, rate of onset and recovery of Compound 6a relative to the parameters for Compound 1 (alphaxalone) was made using tail vein injections in mice. Anesthetic evaluations were performed in 7-8 week-old BALB/C mice, weighing approximately 20 g. Steroids were dissolved in 22.5% (w/v) 2-hydroxypropyl-β-cyclodextrin solution (Sigma-Aldrich) at a concentration of 1.6 mg/ml or 3.2 mg/ml and injected through the tail vein in volumes of 5 μl/g body weight. Doses (8 or 16 mg/kg) were calculated according to body weight. Animals were placed prone as soon as they stopped moving. Loss of LRR was defined as inability of mice to right themselves within 5 seconds after being placed in a prone position. Sleep time was defined as the time from when the mice displayed LRR until they were able to right themselves. Animals were placed on a warming blanket during the time that they were anesthetized. Each dose was administered to three or four mice and the results are presented as mean±standard error of the mean.

Figure 6:
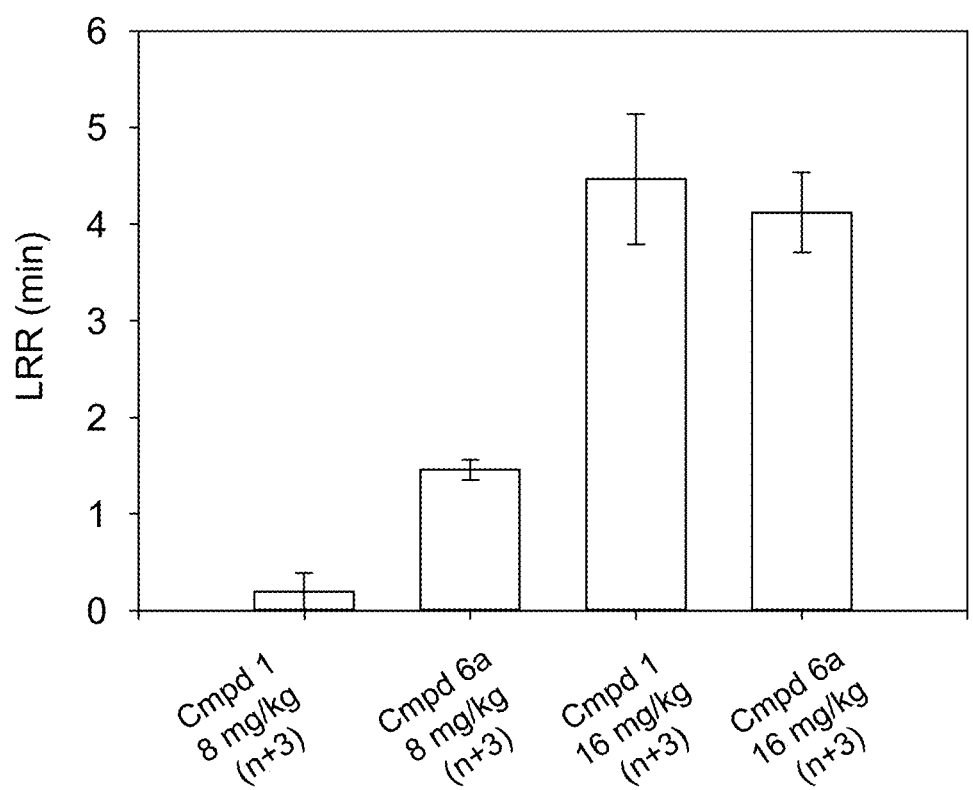
FIG. 6 is a graph illustrating the duration of anesthesia induced by tail vein injection of Compounds 1 and 6a into mice. (The steroids were dissolved in 22.5% aqueous 2-(hydroxypropyl)-β-cyclodextrin.)
Figure 7:
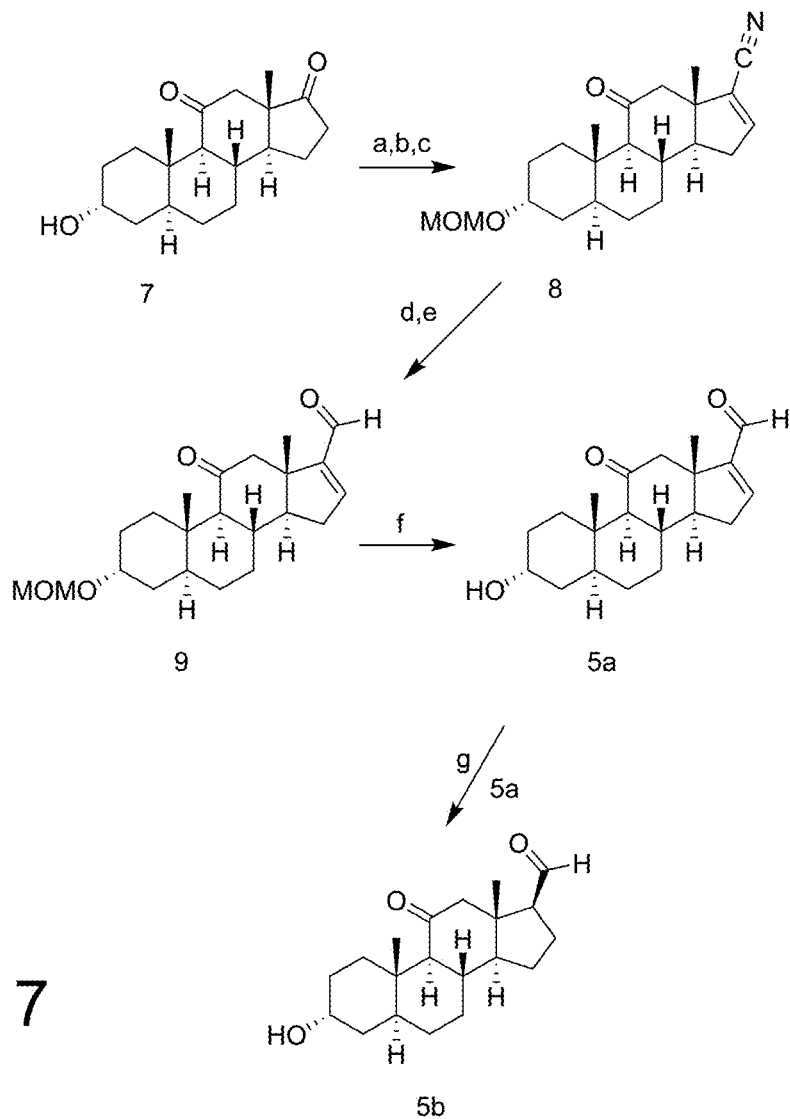
FIG. 7 is synthetic scheme 1 for the preparation of compound 5b.
Figure 8:
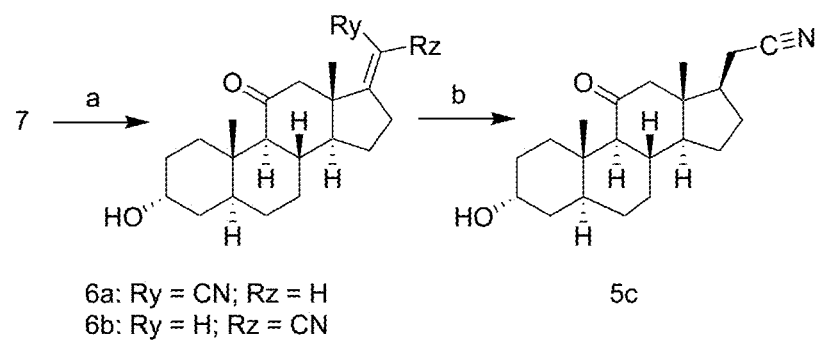
FIG. 8 is synthetic scheme 2 for the preparation of compound 5c.
Figure 9:
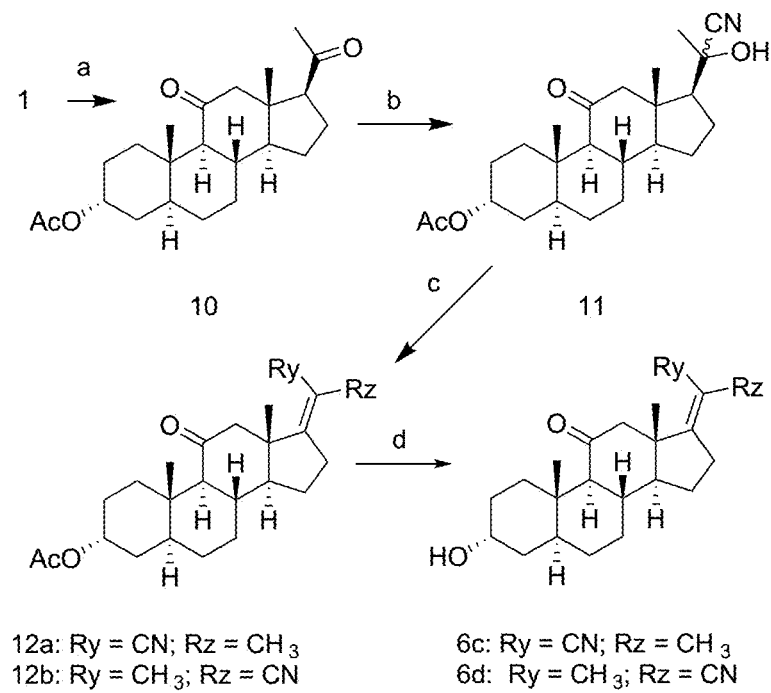
FIG. 9 is synthetic scheme 3 for the preparation of compounds 6c and 6d.
Figure 10:
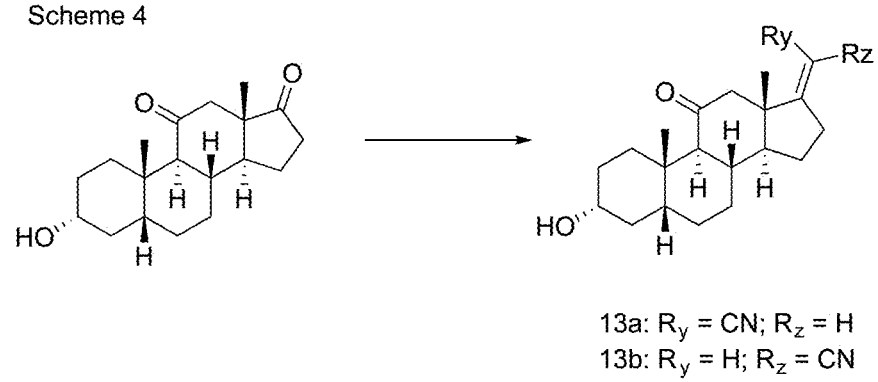
FIG. 10 is synthetic scheme 4 for the preparation of compound 13a and 13b.
Figure 11:
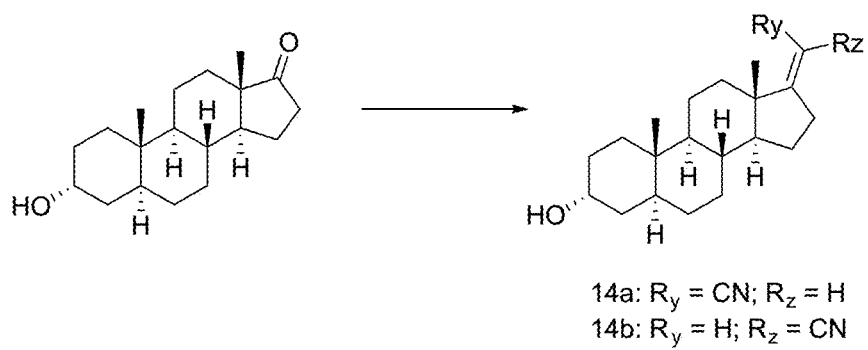
FIG. 11 is synthetic scheme 5 for the preparation of compounds 14a and 14b.
Figure 12:
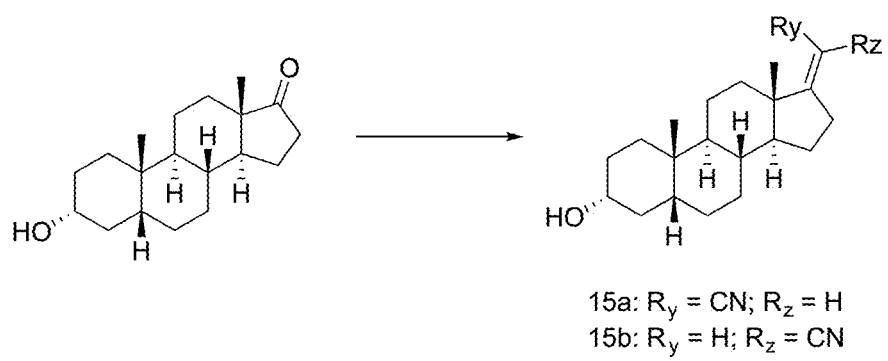
FIG. 12 is synthetic scheme 6 for the preparation of compounds 15a and 15b.
Figure 13:
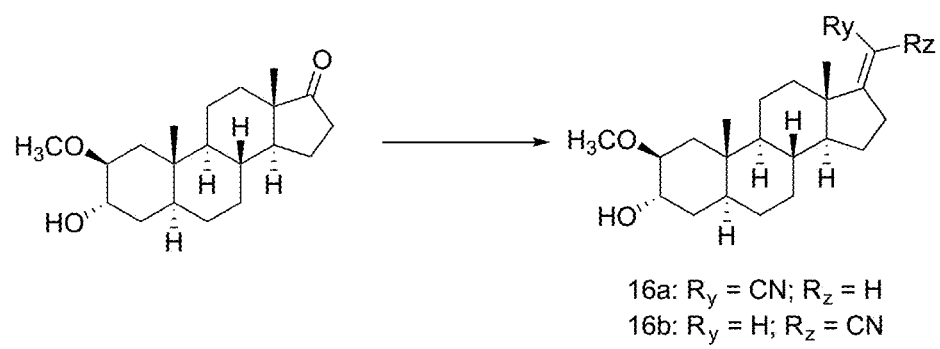
FIG. 13 is synthetic scheme 7 for the preparation of compounds 16a and 16b.
Figure 14:
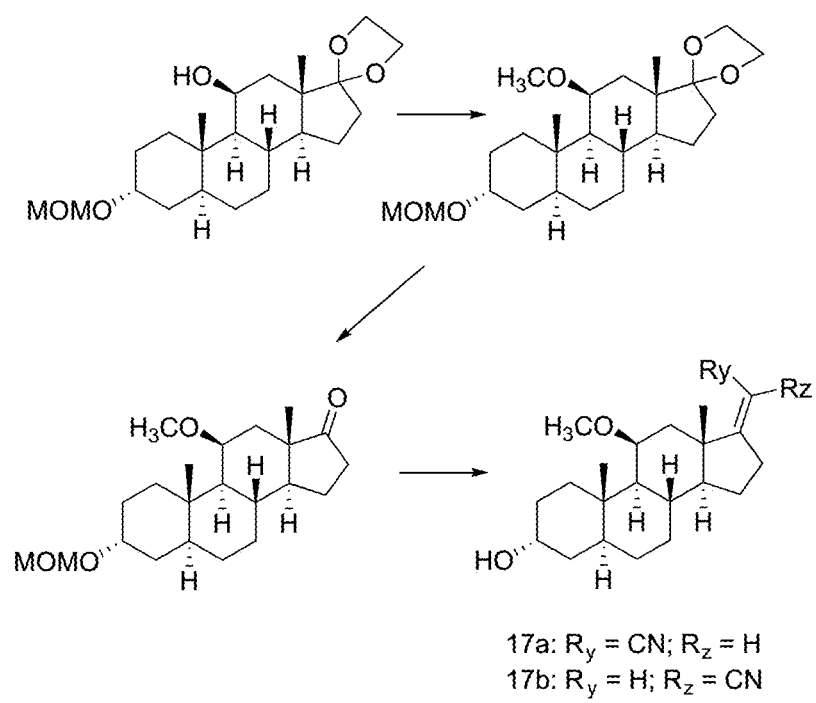
FIG. 14 is synthetic scheme 8 for the preparation of compounds 17a and 17b.

The duration of anesthesia, defined as loss of righting reflex, observed for the two steroids is shown in FIG. 6. Alphaxalone (compound 1) caused very brief anesthesia at a dose of 8 mg/kg. At a dose of 16 mg/kg, alphaxalone caused an immediate loss of righting reflex that lasted for about 4 min. Recovery was characterized by a rapid progression over a period of about 1-2 min from an initial return of leg movement followed to righting and subsequent walking around the cage.

Compound 6a was an anesthetic at a dose of 8 mg/kg. Loss of movement and righting reflex occurred in about 10-25 sec and lasted for about 1.5 min. At a dose of 16 mg/kg, Compound 6a caused an immediate loss of righting reflex that lasted on average about 4 min. The behavioral pattern of recovery for mice injected with either dose of steroid 6a was not distinguishable from the pattern observed for the mice injected with 16 mg/kg of alphaxalone.

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A compound of Formula (I):

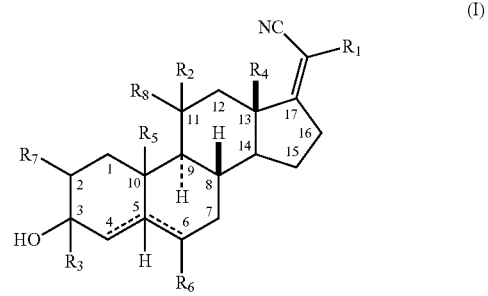

or a pharmaceutically acceptable salt thereof;
wherein:
R$_1$ is H;
R$_2$ is =O, H, or OR$_a$, where R$_a$ is selected from H, optionally substituted C$_1$-C$_4$ alkyl, or optionally substituted aryl, with the proviso that when R$_2$ is =O, R$_8$ is not present;
R$_3$ is H, optionally substituted C$_1$-C$_4$ alkyl, optionally substituted C$_2$-C$_4$ alkene, optionally substituted C$_2$-C$_4$ alkyne, or optionally substituted aryl;
R$_4$ and R$_5$ are each independently selected from H and unsubstituted C$_1$-C$_4$ alkyl;
R$_6$ is H, optionally substituted C$_1$-C$_4$ alkyl, optionally substituted C$_1$-C$_4$ alkoxy;

$R_7$ is H, optionally substituted $C_1$-$C_4$ alkoxy, or an optionally substituted morpholinyl ring;

$R_8$, when present, is H or optionally substituted $C_1$-$C_4$ alkyl; and,

- - - denotes an optional, additional C—C bond, resulting in either a C=C bond between $C_4$-$C_5$ or $C_5$-$C_6$, with the proviso that when present, the $C_5$—H substituent is not present and further with the provisos:

(1) that when the C=C bond is not resent between $C_4$-$C_5$ or $C_5$-$C_6$ and $R_3$ is H, $R_2$ is =O, or $OR_a$, where $R_a$ is selected from H, optionally substituted $C_1$-$C_4$ alkyl, or optionally substituted aryl; or, (2) that when the C=C bond is not resent between $C_4$-$C_5$ or $C_5$-$C_6$ and $R_3$ is H, $R_2$ is H, $R_8$ is H and $R_7$ is optionally substituted $C_1$-$C_4$ alkoxy or an optionally substituted morpholinyl ring;

wherein the $C_3$—OH group is in the alpha configuration and the $C_3$-$R_3$ group is in the beta configuration with the proviso that the compounds

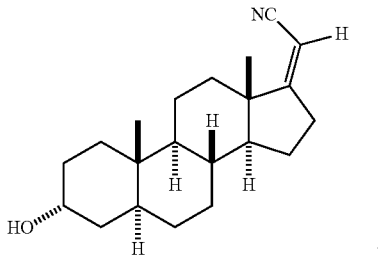

and

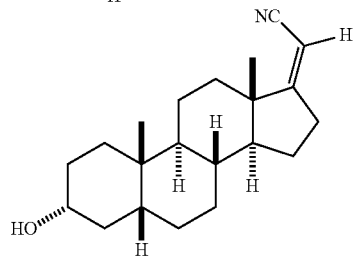

are excluded.

2. The compound of claim 1, wherein the $R_3$ group is selected from the group consisting of H, methyl, and trifluoromethyl.

3. The compound of claim 1, wherein $R_7$ is selected from the group consisting of H, methoxy, ethoxy, and an optionally morpholinyl ring.

4. The compound of claim 1, wherein $R_5$ is methyl.

5. The compound of claim 1, wherein $R_2$ is =O, methoxy or H.

6. The compound of claim 1 of Formula (I-a):

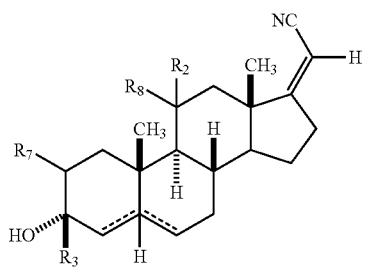

(I-a)

or a pharmaceutically acceptable salt thereof.

7. The compound of claim 1 of Formula (I-j):

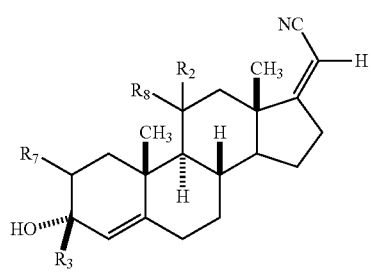

(I-j)

or a pharmaceutically acceptable salt thereof.

8. The compound of claim 1 of Formula (I-k):

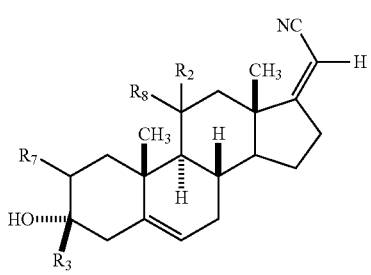

(I-k)

or a pharmaceutically acceptable salt thereof.

9. The compound of claim 1 selected from the group consisting of:

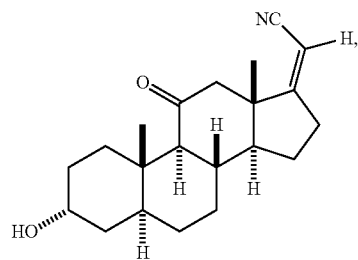

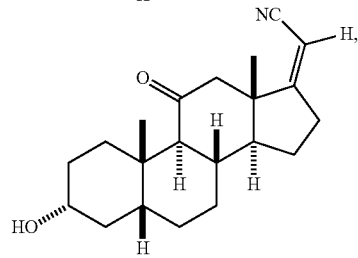

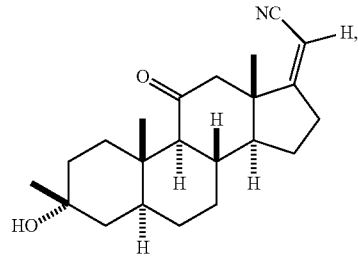

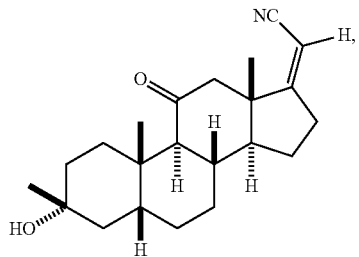
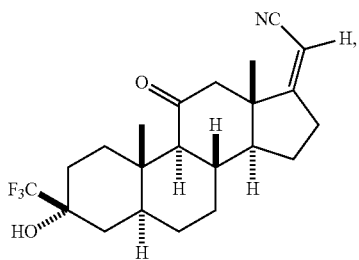
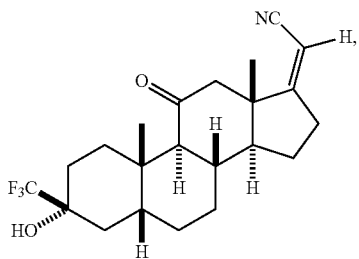
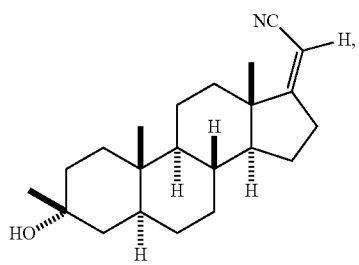
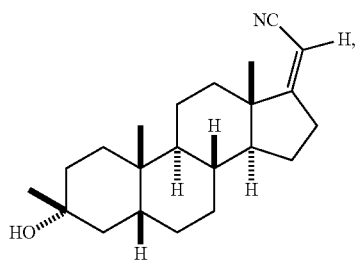
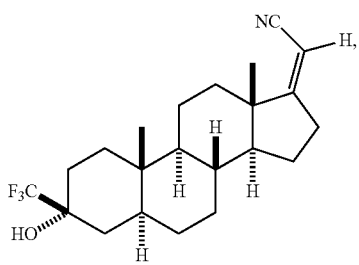
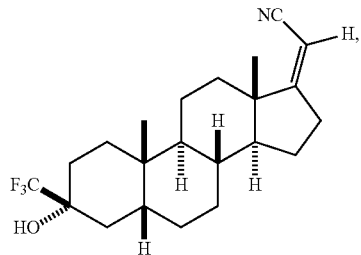
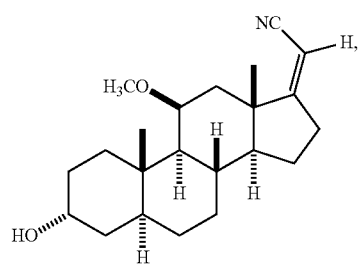
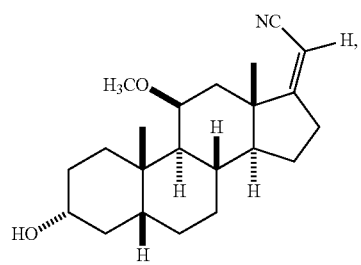
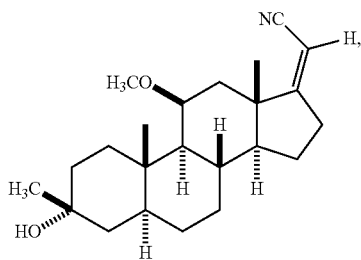
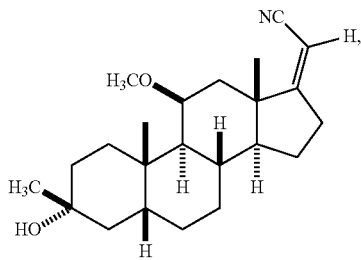
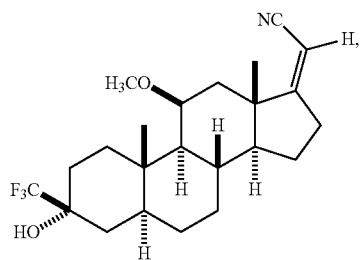

-continued

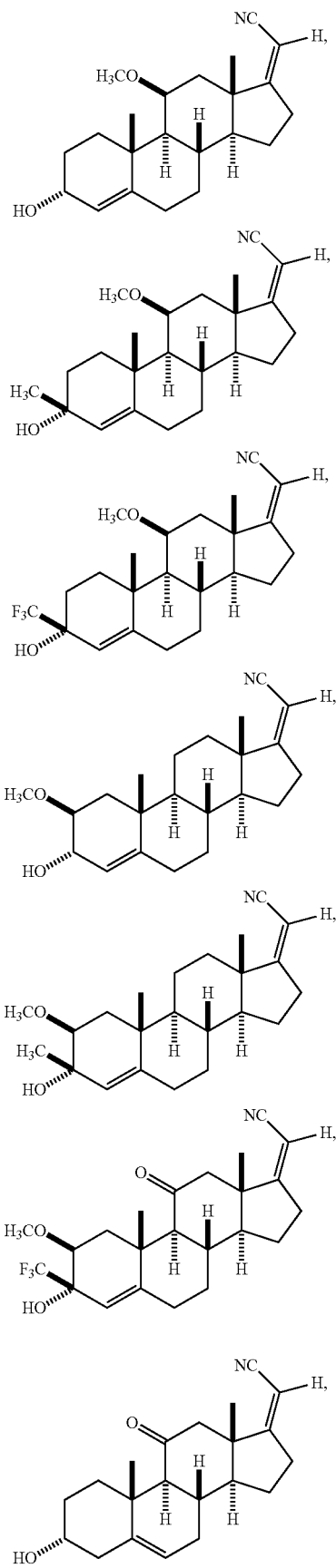
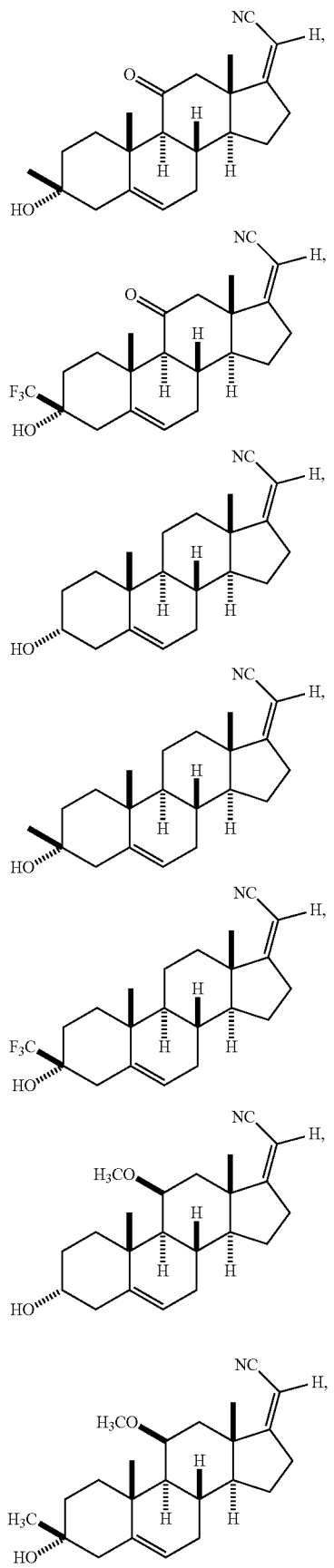

-continued
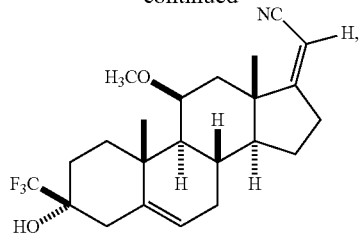
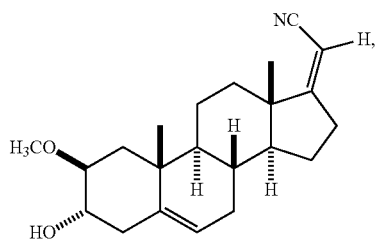
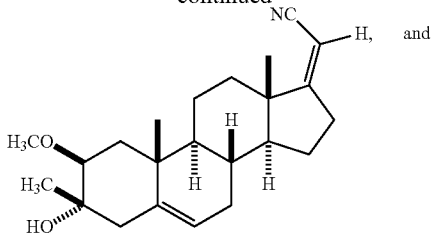
and pharmaceutically acceptable salts thereof.
* * * * *